(12) United States Patent
Jimenez et al.

(10) Patent No.: US 9,723,913 B2
(45) Date of Patent: *Aug. 8, 2017

(54) ORAL CARE SYSTEM, KIT AND METHOD

(71) Applicant: COLGATE-PALMOLIVE COMPANY, New York, NY (US)

(72) Inventors: Eduardo Jimenez, Manalapan, NJ (US); Robert Moskovich, East Brunswick, NJ (US); Sharon Kennedy, Randallstown, MD (US); John Gatzemeyer, Hillsborough, NJ (US); Joachim Storz, Zell am See (AT); Raimund Klausegger, Vienna (AT)

(73) Assignee: COLGATE-PALMOLIVE COMPANY, New York, NY (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/878,118

(22) Filed: Oct. 8, 2015

(65) Prior Publication Data

US 2016/0022023 A1    Jan. 28, 2016

Related U.S. Application Data

(63) Continuation of application No. 14/289,824, filed on May 29, 2014, now Pat. No. 9,179,765, which is a (Continued)

(51) Int. Cl.
*A46B 11/00* (2006.01)
*A46B 15/00* (2006.01)
(Continued)

(52) U.S. Cl.
CPC ............ *A46B 11/0055* (2013.01); *A46B 9/04* (2013.01); *A46B 11/0006* (2013.01);
(Continued)

(58) Field of Classification Search
CPC .......... A46B 11/00; A46B 15/00; A46B 17/08
(Continued)

(56) References Cited

U.S. PATENT DOCUMENTS 64,732 A    5/1867    Wylie
261,456 A    7/1882    Hoffman
(Continued)

FOREIGN PATENT DOCUMENTS

CN    201025977    2/2008
DE    2725495    12/1977
(Continued)

OTHER PUBLICATIONS

ISR and Written Opinion for PCT/US2010/060867 mailed on Oct. 14, 2011.
(Continued)

*Primary Examiner* — David Walczak
*Assistant Examiner* — Joshua Wiljanen

(57) ABSTRACT

An oral care system that includes an oral care implement and a dispenser, an oral care method, and a method of applying an oral care agent to an oral surface. In one embodiment, the invention may be a method of applying an oral care agent to an oral surface that includes: providing a kit comprising a toothbrush and a dispenser containing an oral care agent; removing the dispenser from kit; and applying the oral care agent to an oral surface using the dispenser.

10 Claims, 23 Drawing Sheets

Related U.S. Application Data continuation of application No. 13/518,424, filed as application No. PCT/US2009/069402 on Dec. 23, 2009, now Pat. No. 8,757,912.

(51) Int. Cl.
  *A46B 17/08* (2006.01)
  *A46B 9/04* (2006.01)
  *A61C 19/06* (2006.01)

(52) U.S. Cl.
  CPC ...... *A46B 11/0041* (2013.01); *A46B 11/0065* (2013.01); *A61C 19/063* (2013.01); *A61C 19/066* (2013.01); *A46B 15/00* (2013.01); *A46B 17/08* (2013.01); *A46B 2200/1066* (2013.01)

(58) Field of Classification Search
  USPC ..... 401/37, 38, 39, 118, 123, 126, 127, 129, 401/137, 138; 132/308, 311; 206/229
  See application file for complete search history.

(56) References Cited

U.S. PATENT DOCUMENTS

| | | |
|---|---|---|
| 1,244,324 A | 10/1917 | Hackley |
| 1,292,416 A | 1/1919 | Auld |
| 1,546,516 A | 7/1925 | Smith |
| 1,555,064 A | 9/1925 | La Mothe |
| 1,668,511 A | 5/1928 | McLaughlin |
| 1,701,030 A | 2/1929 | Collins |
| 1,746,474 A | 2/1930 | Hogner |
| 1,913,528 A | 6/1933 | White |
| 1,975,723 A | 10/1934 | Johnssen |
| 2,105,709 A | 1/1938 | Vioette |
| D134,723 S | 1/1943 | Riksheim |
| 2,356,874 A | 8/1944 | Nageotte |
| 2,437,769 A | 3/1948 | Traylor |
| 2,445,571 A | 7/1948 | Fuston |
| 2,448,033 A | 8/1948 | Kruck |
| 2,521,882 A | 9/1950 | Swift et al. |
| 2,541,949 A | 2/1951 | Thacker et al. |
| 2,579,899 A | 12/1951 | Burrows |
| 2,637,060 A | 5/1953 | Cowan |
| 2,670,881 A | 3/1954 | Sjoblom |
| 2,676,568 A | 4/1954 | Maczynski |
| 2,718,299 A | 9/1955 | Atwater et al. |
| 2,771,858 A | 11/1956 | Cribbs et al. |
| 2,800,899 A | 7/1957 | Barron |
| 2,885,110 A | 5/1959 | Tregilgas |
| 2,885,116 A | 5/1959 | Tregilgas |
| 3,108,687 A | 10/1963 | Dayton |
| 3,148,684 A | 9/1964 | Keeler |
| 3,181,539 A | 5/1965 | Aston |
| 3,187,758 A | 6/1965 | Eklund |
| 3,215,320 A | 11/1965 | Heisler et al. |
| 3,293,749 A | 12/1966 | George et al. |
| 3,296,642 A | 1/1967 | Aylott |
| 3,358,699 A | 12/1967 | Bau |
| 3,359,991 A | 12/1967 | Spatz |
| 3,359,992 A | 12/1967 | Cishek et al. |
| 3,378,176 A | 4/1968 | Snyder |
| 3,406,694 A | 10/1968 | Odence |
| 3,468,612 A | 9/1969 | Aston |
| 3,683,924 A | 8/1972 | Louie |
| 3,842,850 A | 10/1974 | Sanders |
| 3,910,706 A | 10/1975 | Del Bon |
| 3,986,645 A | 10/1976 | Baldwin et al. |
| 4,275,750 A | 6/1981 | Clark |
| 4,277,194 A | 7/1981 | Smith |
| 4,296,518 A | 10/1981 | Furrier et al. |
| 4,323,157 A | 4/1982 | Idec |
| 4,331,267 A | 5/1982 | Duncan et al. |
| 4,340,367 A | 7/1982 | Vadas et al. |
| 4,350,712 A | 9/1982 | Kocharian et al. |
| 4,384,645 A | 5/1983 | Manfredi |
| 4,413,760 A | 11/1983 | Paton |
| 4,506,810 A | 3/1985 | Goncalves |
| 4,527,574 A | 7/1985 | Manfredi |
| 4,573,820 A | 3/1986 | Kirchhoff |
| 4,582,059 A | 4/1986 | Tiwari |
| 4,641,766 A | 2/1987 | Vlasich |
| 4,655,372 A | 4/1987 | Ross et al. |
| 4,659,327 A | 4/1987 | Bennett et al. |
| 4,662,385 A | 5/1987 | Schefer |
| 4,763,815 A | 8/1988 | Von Schuckmann et al. |
| 4,767,032 A | 8/1988 | Smith |
| 4,776,717 A | 10/1988 | Iizuka et al. |
| 4,808,022 A | 2/1989 | Iizuka et al. |
| 4,826,341 A | 5/1989 | Kwak |
| 4,874,117 A | 10/1989 | Kay et al. |
| 4,879,781 A | 11/1989 | Desimone |
| 4,886,186 A | 12/1989 | Andris |
| 4,887,924 A | 12/1989 | Green |
| 4,892,427 A | 1/1990 | Ford |
| D310,308 S | 9/1990 | Wolsey |
| 4,954,000 A | 9/1990 | Gueret |
| 4,997,299 A | 3/1991 | Ohba |
| 5,000,356 A | 3/1991 | Johnson et al. |
| 5,011,317 A | 4/1991 | Gueret |
| 5,016,782 A | 5/1991 | Pfanstiel |
| 5,018,892 A | 5/1991 | Krueckel et al. |
| 5,066,155 A | 11/1991 | English et al. |
| 5,156,479 A | 10/1992 | Iizuka |
| 5,199,807 A | 4/1993 | Uchida |
| 5,217,475 A | 6/1993 | Kuber |
| 5,234,136 A | 8/1993 | Kopis |
| 5,249,876 A | 10/1993 | Hattman |
| 5,294,205 A | 3/1994 | Moeck et al. |
| 5,336,005 A | 8/1994 | Moeck et al. |
| 5,423,623 A | 6/1995 | Bakic |
| 5,454,660 A | 10/1995 | Sakurai et al. |
| 5,540,361 A | 7/1996 | Fattori |
| 5,547,302 A | 8/1996 | Dornbusch et al. |
| 5,560,518 A | 10/1996 | Catterall et al. |
| 5,569,278 A | 10/1996 | Persad |
| 5,573,341 A | 11/1996 | Iaia |
| 5,697,531 A | 12/1997 | Fattori |
| 5,709,004 A | 1/1998 | Paduano et al. |
| 5,725,133 A | 3/1998 | Iaia |
| 5,733,058 A | 3/1998 | Hofmann |
| 5,765,573 A | 6/1998 | Gueret |
| 5,772,347 A | 6/1998 | Gueret |
| 5,791,801 A | 8/1998 | Miller |
| 5,803,640 A | 9/1998 | Nakajima et al. |
| 5,827,002 A | 10/1998 | Nakajima |
| 5,827,308 A | 10/1998 | Thakur et al. |
| 5,839,622 A | 11/1998 | Bicknell et al. |
| 5,851,079 A | 12/1998 | Horstman et al. |
| 5,860,572 A | 1/1999 | Harrold et al. |
| 5,879,095 A | 3/1999 | Gueret |
| 5,893,860 A | 4/1999 | Ripich et al. |
| 5,916,228 A | 6/1999 | Ripich et al. |
| 5,941,254 A | 8/1999 | Heler |
| 5,955,114 A | 9/1999 | Llanos |
| 5,996,850 A | 12/1999 | Morali et al. |
| 6,015,293 A | 1/2000 | Rimkus |
| 6,039,053 A | 3/2000 | Turrentine |
| 6,056,763 A | 5/2000 | Parsons |
| 6,059,570 A | 5/2000 | Dragan et al. |
| 6,070,598 A | 6/2000 | Gueret |
| 6,071,026 A | 6/2000 | Martinez et al. |
| 6,082,918 A | 7/2000 | Gueret |
| 6,086,276 A | 7/2000 | Gueret |
| 6,200,055 B1 | 3/2001 | Fusaro, Jr. |
| 6,202,247 B1 | 3/2001 | Lorenz, Jr. |
| 6,210,061 B1 | 4/2001 | Johnson |
| 6,213,662 B1 | 4/2001 | Aljanedi |
| 6,220,773 B1 | 4/2001 | Wiegner et al. |
| 6,224,573 B1 | 5/2001 | Yeager et al. |
| 6,227,209 B1 | 5/2001 | Kim et al. |
| 6,238,117 B1 | 5/2001 | Griebel et al. |
| 6,290,417 B1 | 9/2001 | Kaminski |
| 6,325,076 B1 | 12/2001 | Ramirez |

(56) References Cited

U.S. PATENT DOCUMENTS

| | | |
|---|---|---|
| 6,331,085 B1 | 12/2001 | Schrepf et al. |
| 6,345,629 B1 | 2/2002 | Vives |
| 6,363,949 B1 | 4/2002 | Brown |
| 6,368,001 B1 | 4/2002 | Roeder |
| 6,398,439 B1 | 6/2002 | Szekely |
| 6,406,694 B1 | 6/2002 | LaRosa |
| 6,440,149 B1 | 8/2002 | Potti |
| 6,450,716 B1 | 9/2002 | Szekely |
| 6,475,172 B1 | 11/2002 | Hall |
| 6,488,427 B1 | 12/2002 | Breidenbach et al. |
| 6,592,281 B2 | 7/2003 | Clark et al. |
| 6,607,323 B2 | 8/2003 | Breidenbach et al. |
| 6,647,581 B1 | 11/2003 | Persad et al. |
| 6,672,783 B1 | 1/2004 | Licata et al. |
| 6,688,317 B2 | 2/2004 | Gueret |
| 6,688,793 B2 | 2/2004 | Goyet |
| 6,688,796 B1 | 2/2004 | Liu |
| 6,745,781 B2 | 6/2004 | Gueret |
| 6,746,170 B2 | 6/2004 | Delage |
| 6,752,558 B1 | 6/2004 | Hsu |
| 6,824,018 B1 | 11/2004 | Eaddy et al. |
| 6,866,438 B2 | 3/2005 | Bauer et al. |
| 6,880,999 B2 | 4/2005 | Biegel et al. |
| 6,918,511 B1 | 7/2005 | Spatz et al. |
| 6,923,587 B2 | 8/2005 | Lee |
| 6,957,753 B2 | 10/2005 | Tani |
| 7,029,484 B2 | 4/2006 | Ripich |
| 7,040,893 B2 | 5/2006 | Fischer |
| 7,044,671 B2 | 5/2006 | Parikh et al. |
| 7,051,642 B2 | 5/2006 | Kageyama |
| 7,055,527 B2 | 6/2006 | Tien |
| 7,086,564 B1 | 8/2006 | Corrigan |
| 7,086,796 B2 | 8/2006 | Severa |
| 7,089,564 B2 | 8/2006 | Chen et al. |
| 7,112,003 B2 | 9/2006 | Frison |
| 7,114,505 B2 | 10/2006 | Bauer et al. |
| 7,143,462 B2 | 12/2006 | Hohlbein |
| 7,144,175 B2 | 12/2006 | Biegel |
| 7,168,435 B2 | 1/2007 | Vieu et al. |
| 7,192,212 B2 | 3/2007 | Gutberlet et al. |
| 7,201,527 B2 | 4/2007 | Thorpe et al. |
| 7,210,870 B2 | 5/2007 | Breidenbach et al. |
| 7,217,054 B2 | 5/2007 | Noguchi |
| 7,226,231 B2 | 6/2007 | Py et al. |
| 7,237,974 B2 | 7/2007 | Pfenniger et al. |
| 7,237,975 B2 | 7/2007 | Noguchi |
| 7,303,348 B2 | 12/2007 | Phipps et al. |
| 7,309,184 B2 | 12/2007 | Butcher et al. |
| 7,309,185 B2 | 12/2007 | Thorpe et al. |
| 7,347,360 B2 | 3/2008 | Lasch et al. |
| 7,374,360 B1 | 5/2008 | Szekely |
| 7,396,180 B2 | 7/2008 | Bugla et al. |
| 7,401,373 B2 | 7/2008 | Tybinkowski et al. |
| 7,461,988 B2 | 12/2008 | Albisetti |
| 7,465,113 B2 | 12/2008 | Gueret |
| 7,474,048 B2 | 1/2009 | Forrest et al. |
| 7,481,591 B2 | 1/2009 | Dumler |
| 7,520,406 B2 | 4/2009 | Jaichandra et al. |
| 7,557,936 B2 | 7/2009 | Dickinson |
| 7,614,811 B2 | 11/2009 | Kaufman et al. |
| 7,641,411 B2 | 1/2010 | Biegel |
| 7,651,291 B2 | 1/2010 | Py et al. |
| 7,665,923 B2 | 2/2010 | Py et al. |
| 7,823,593 B2 | 11/2010 | Gueret |
| 8,075,216 B2 | 12/2011 | Gatzemeyer et al. |
| 8,425,133 B2 | 4/2013 | Grez et al. |
| 2002/0054783 A1 | 5/2002 | Gueret |
| 2002/0073496 A1 | 6/2002 | Kim |
| 2003/0057236 A1 | 3/2003 | Delage |
| 2004/0028456 A1 | 2/2004 | Giraldo |
| 2004/0092981 A1 | 5/2004 | Barlow et al. |
| 2004/0237996 A1 | 12/2004 | Fischer et al. |
| 2004/0240928 A1 | 12/2004 | Trocino |
| 2005/0006409 A1 | 1/2005 | Ganzeboom |
| 2005/0026774 A1 | 2/2005 | Nolan |
| 2005/0036821 A1 | 2/2005 | Pfenniger et al. |
| 2005/0069372 A1 | 3/2005 | Hohlbein et al. |
| 2005/0199655 A1 | 9/2005 | Petit |
| 2006/0058821 A1 | 3/2006 | Jansheski |
| 2006/0133885 A1 | 6/2006 | Kaminski |
| 2006/0207627 A1 | 9/2006 | Thorpe et al. |
| 2006/0233588 A1 | 10/2006 | Gueret |
| 2006/0269351 A1 | 11/2006 | McAfee |
| 2006/0269354 A1 | 11/2006 | Lane |
| 2006/0272666 A1 | 12/2006 | Wyatt et al. |
| 2006/0275225 A1 | 12/2006 | Prencipe et al. |
| 2007/0007302 A1 | 1/2007 | Jaichandra et al. |
| 2007/0079845 A1 | 4/2007 | Gueret |
| 2007/0227553 A1 | 10/2007 | Gueret |
| 2007/0231055 A1 | 10/2007 | Albisetti |
| 2007/0292194 A1 | 12/2007 | Albisetti et al. |
| 2008/0063464 A1 | 3/2008 | Prague |
| 2008/0089733 A1 | 4/2008 | Lochak |
| 2008/0101850 A1 | 5/2008 | Wojcik et al. |
| 2008/0189888 A1 | 8/2008 | Hohlbein |
| 2008/0274066 A1 | 11/2008 | Montgomery |
| 2009/0074679 A1 | 3/2009 | Silverman |
| 2009/0254055 A1 | 10/2009 | Clarke |
| 2009/0261007 A1 | 10/2009 | Sanchez |
| 2009/0288262 A1 | 11/2009 | Hall |
| 2009/0317432 A1 | 12/2009 | Kergosien |
| 2010/0168638 A1 | 7/2010 | Korogi et al. |
| 2010/0240013 A1 | 9/2010 | Levine |
| 2011/0308030 A1 | 12/2011 | Jimenez et al. |
| 2012/0114410 A1 | 5/2012 | Jimenez et al. |
| 2012/0163902 A1 | 6/2012 | Jimenez et al. |

FOREIGN PATENT DOCUMENTS

| | | |
|---|---|---|
| DE | 3832224 | 8/1989 |
| DE | 29613012 | 10/1996 |
| EP | 1506726 | 2/2005 |
| FR | 850458 | 12/1939 |
| FR | 907669 | 3/1946 |
| FR | 1596074 | 6/1970 |
| FR | 2597734 | 10/1987 |
| GB | 666082 | 2/1952 |
| GB | 2085717 | 5/1982 |
| GB | 2280361 | 2/1995 |
| JP | 48-093167 | 12/1973 |
| NL | 2002311 | 6/2010 |
| WO | WO 93/03648 | 3/1993 |
| WO | WO 98/09572 | 3/1998 |
| WO | WO 98/18695 | 5/1998 |
| WO | WO 01/00103 | 1/2001 |
| WO | WO 02/17967 | 3/2002 |
| WO | WO 2004/112637 | 12/2004 |
| WO | WO 2008/062935 | 5/2008 |
| WO | WO 2009/151455 | 12/2009 |
| WO | WO 2011/035011 | 3/2011 |
| WO | WO 2011/078864 | 6/2011 |
| WO | WO 2011/079027 | 6/2011 |
| WO | WO 2011/079028 | 6/2011 |
| WO | WO 2012/082102 | 6/2012 |
| WO | WO 2012/082183 | 6/2012 |
| WO | WO 2012/082185 | 6/2012 |

OTHER PUBLICATIONS

ISR and Written Opinion for PCT/US2011/023356 mailed on Oct. 21, 2011.

ISR and Written Opinion for PCT/US2011/045010 mailed on Nov. 25, 2011.

ISR and Written Opinion for PCT/US2010/060874 mailed on Jan. 11, 2012.

ISR and Written Opinion for PCT/US2009/069402 mailed on Jul. 23, 2010.

ISR and Written Opinion for PCT/US2009/069408 mailed on Jul. 23, 2010.

ISR and Written Opinion for PCT/US2010/060881 mailed on May 16, 2011.

ISR and Written Opinion for PCT/US2010/049102 mailed on Jun. 7, 2011.

(56) References Cited

OTHER PUBLICATIONS

ISR and Written Opinion for PCT/US2010/060861 mailed on Jun. 8, 2011.
ISR and Written Opinion for PCT/US2010/060105 mailed on Aug. 30, 2011.
ISR and Written Opinion for PCT/US2010/060877 mailed on Oct. 7, 2011.
ISR and Written Opinion for PCT/US2011/046132 mailed on Dec. 1, 2011.
Written Opinion for PCT/US2009/069402 mailed on Dec. 16, 2011.
Written Opinion for PCT/US2009/069408 mailed on Dec. 16, 2011.
Written Opinion for PCT/US2010/060881 mailed on Dec. 28, 2011.

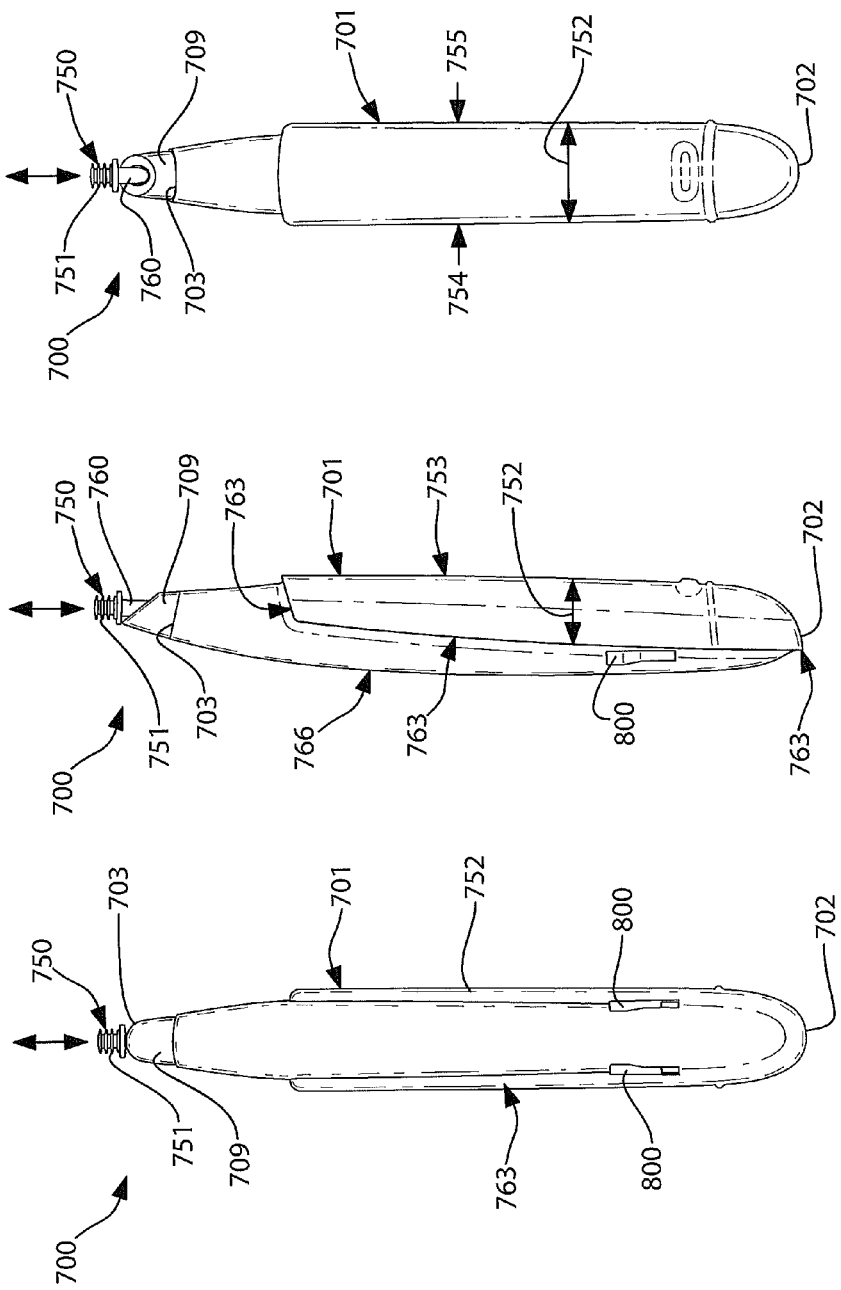

ORAL CARE SYSTEM, KIT AND METHOD

CROSS-REFERENCE TO RELATED APPLICATIONS

This application is a continuation of U.S. patent application Ser. No. 14/289,824, filed on May 29, 2014, now allowed, which is a continuation of U.S. patent application Ser. No. 13/518,424, filed on Jun. 22, 2012, now U.S. Pat. No. 8,757,912, issued Jun. 24, 2014, which is a national stage entry under 35 U.S.C. §371 of International Patent Application No. PCT/US2009/069402, filed Dec. 23, 2009, the entireties of which are incorporated herein by reference.

BACKGROUND

Oral care products or agents are applied in different ways. For example, without limitation, a common technique used for tooth whitening products is to cast an impression of a person's teeth and provide a tray of the shape of this impression. A person then only needs to add a whitening composition to the tray and to apply the tray to his/her teeth. This is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to ones teeth. After a few treatments the teeth gradually whiten.

A problem with existing brushing techniques is that saliva in the mouth contains the enzyme catalase. This enzyme will catalyze the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative effect on the whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen.

A more portable, compact and convenient way to store oral care products, and to dispense and apply those oral care products to oral surfaces is desired.

SUMMARY

Embodiments of the present invention provide an efficient, compact, and portable oral care system that combines an oral care implement such as a toothbrush with an oral care product or agent dispenser in a highly portable housing. Advantageously, such embodiments are especially suited for easy transport and/or travel.

Preferred embodiments of the present invention are directed to a toothbrush having an open cavity in its handle that retains a removable dispenser containing an oral care agent reservoir. In some exemplary embodiments, the oral care system includes oral care agents, either active or non-active, that may include whitening agents. The dispenser is detachably docked and stored at least partially within the handle of the toothbrush so that a gripping portion of the dispenser protrudes from the toothbrush for access to a user permitting easy removal and use of the dispenser. The dispenser is completely removable from the toothbrush so that the user can apply the whitening agent to his/her teeth with ease, and then reinsert the dispenser in the toothbrush for convenient storage. The toothbrush removably and non-fixedly secures the dispenser within the handle so that the dispenser can be repetitively removed and reinserted therein. In some embodiments, the dispenser may be adapted to be user-refillable for repeated use.

In one embodiment, an oral care system includes a toothbrush comprising a handle defining a longitudinal axis and having a proximal end, a distal end, and a cantilevered top portion; a head connected to the distal end of the handle; and a dispenser comprising: a longitudinally elongated housing having a distal end with an applicator therein and an opposite proximal end; and a reservoir disposed in the housing for holding an oral care agent, the reservoir in fluid communication with the applicator, wherein the dispenser is removably attached to the top portion of the toothbrush handle.

In another embodiment, a method is provided for dispensing and applying the oral care agent to a surface in the oral cavity of a user. In such embodiment, the invention may be a method of whitening teeth comprising: providing a toothbrush having a handle and a detachable tooth whitening agent dispenser supported by the handle, the dispenser including a reservoir containing a tooth whitening agent; decoupling the dispenser from the handle of the toothbrush; and applying the tooth whitening agent to an oral surface using the dispenser.

In yet another embodiment, the invention may be oral care method comprising: providing a toothbrush having a handle and a head, a plurality of tooth cleaning elements extending from the head, the handle of the toothbrush supporting a detachable dispenser, the dispenser having a reservoir containing a tooth whitening agent; applying a dentifrice to the tooth cleaning elements; inserting the head of the toothbrush into a mouth and contacting teeth within the mouth with the tooth cleaning elements in order to brush the teeth; removing the head of the toothbrush from the mouth; decoupling the dispenser from the handle of the toothbrush; and applying the tooth whitening agent to at least one of the teeth using the dispenser.

In still another embodiment, the invention may be a method of applying an oral care agent to an oral surface comprising: providing a kit comprising at least one toothbrush and a dispenser containing an oral care agent, an applicator coupled to an end of the dispenser; delivering the oral care agent to the applicator; and applying the oral care agent to an oral surface using the applicator.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the preferred embodiments will be described with reference to the following drawings in which like elements are labeled similarly.

FIGS. 23-25 are a top view, side elevation view, and bottom view respectively of the dispenser of the oral care system of FIG. 16.

DETAILED DESCRIPTION

Figure 1:
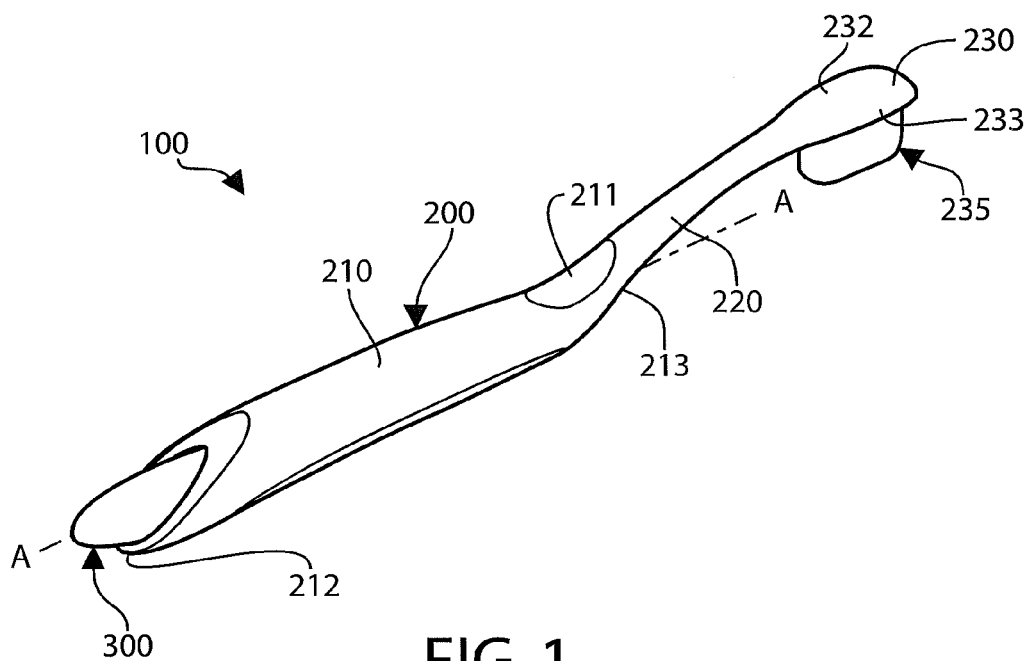
FIG. 1 is a rear perspective view of an oral care system including a toothbrush and oral care agent dispenser according to one embodiment of the present invention.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

In the description of embodiments of the invention disclosed herein, any reference to direction or orientation is merely intended for convenience of description and is not intended in any way to limit the scope of the present invention. Moreover, the features and benefits of the invention are illustrated by reference to preferred embodiments. Accordingly, the invention expressly should not be limited to such preferred embodiments illustrating some possible but non-limiting combination of features that may be provided alone or in other combinations of features; the scope of the invention being defined by the claims appended hereto.

Preferred embodiments of the present invention will now be described with respect to one possible oral care or treatment system. Embodiments of the oral care system may include without limitation the following agents: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of oral care agent and the invention is expressly not limited to any particular oral care system or agent alone.

Figure 2:
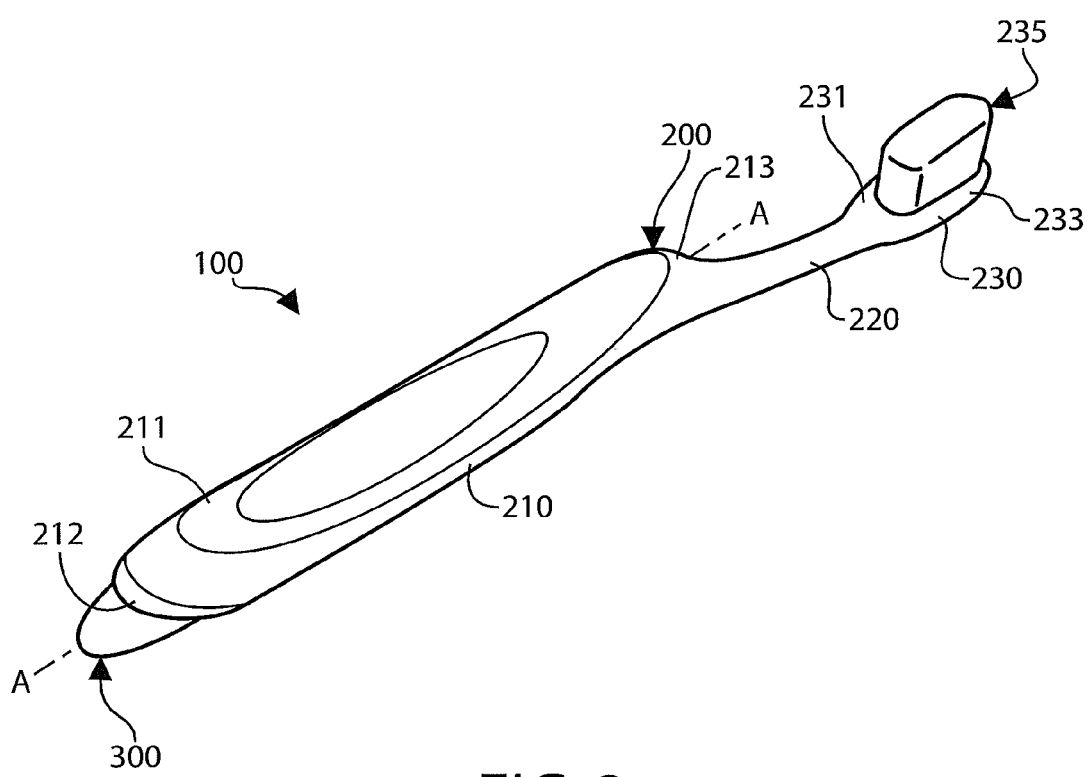
FIG. 2 is a front perspective view of the oral care system of FIG. 1.
Figure 3:
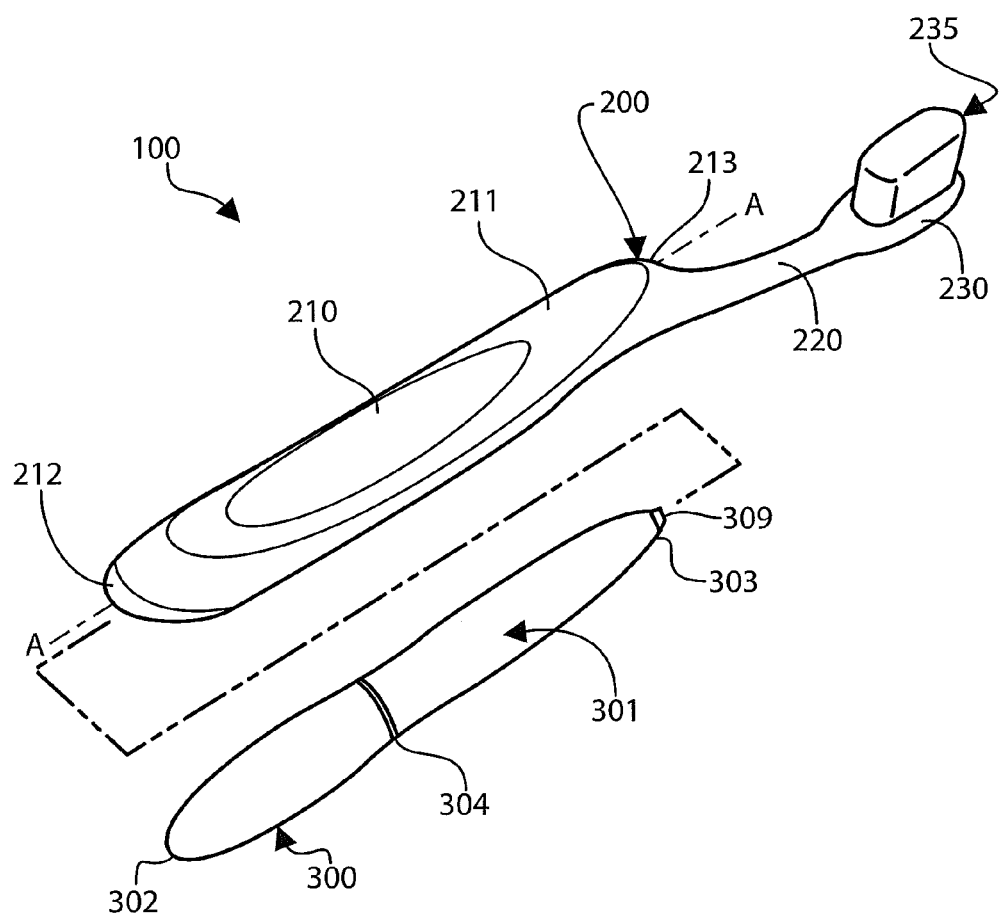
FIG. 3 is a front perspective view of the oral care system of FIG. 1 with the dispenser removed from the toothbrush.

Referring to FIGS. 1-3, an oral care system 100 is illustrated according to one embodiment of the present invention. The oral care system 100 is a compact readily portable self-contained user-friendly system that comprises all of the necessary components and chemistries necessary for a user to perform a desired oral care treatment routine. As will be described in greater detail below, the oral care system 100 in one exemplary embodiment generally takes the form of a modified toothbrush having a removable dispenser disposed at least partially within its handle. Because the dispenser is located within the handle of the toothbrush itself, the oral care system 100 is portable for travel, easy to use, and reduces the amount of required storage space. Furthermore, since the toothbrush and dispenser are housed together, the user is less likely to misplace the dispenser and be more inclined to maintain the oral treatment routine with the dispenser since brushing will remind the user to simply detach and apply the contents of the dispenser.

The oral care system 100 generally comprises a toothbrush 200 and a dispenser 300. While the invention is described herein with respect to the use of a toothbrush as one of the two primary components of the oral care system 100, it is to be understood that other alternate oral care implements can be used within the scope of the invention, including tongue cleaners, tooth polishers and specially designed ansate implements having tooth engaging elements specially designed to increase the effect of the active agent in the dispenser on the teeth. Moreover, while the toothbrush 200 is preferably a manual toothbrush, the toothbrush may be a powered toothbrush in other embodiments of the invention. It is to be understood that the inventive system can be utilized for a variety of intended oral care needs by filling the dispenser 300 with any oral care material, such as an oral care agent that achieves a desired oral effect. In one embodiment, the oral care agent, is preferably free of (i.e., is not) toothpaste as the dispenser is intended to augment not supplant the brushing regimen. The oral care agent and/or its medium can be selected to complement a toothpaste formula, such as by coordinating flavors, colors, aesthetics, or active ingredients.

The toothbrush 200 generally comprises a handle portion 210, a neck portion 220 and a head portion 230. The handle 210 provides the user with a mechanism by which he/she can readily grip and manipulate the toothbrush 100. The handle 210 may be formed of many different shapes, sizes, materials and a variety of manufacturing methods that are well-known to those skilled in the art, so long as it can house the dispenser 300 therein as described in detail below. If desired, the handle 210 may include a suitable textured grip 211 made of soft elastomeric material. The handle 210 can be a single or multi-part construction. The handle 210 extends from a proximal end 212 to a distal end 213 along a longitudinal axis A-A. As will be described in greater detail below with respect to FIG. 6, a cavity 240 is formed within the handle 210. An opening 215 is provided at the proximal end 212 of the handle 210 that provides a passageway into the cavity 240 through which the dispenser 300 can be inserted and retracted. While the opening 215 is located at the proximal end 212 of the handle in the exemplified embodiment, the opening may be located at other positions on the handle 210 in other embodiments of the invention. For example, the opening 215 may be located on a longitudinal surface of the handle 210 and be elongated to provide sufficient access to the cavity 240, as further described herein with respect to an alternative embodiment shown in FIG. 16.

The handle 210 transitions into the neck 220 at the distal end 213. While the neck 220 generally has a smaller transverse cross-sectional area than the handle 220, the invention is not so limited. The neck 220 is merely the transition region between the handle 210 and the head 230 and can conceptually be considered as a portion of the handle 210. In this manner, the head 230 is connected to the distal end 213 of the handle 210 (via the neck 220).

The head 230 and handle 220 of the toothbrush 200 are preferably formed as a single unitary structure using a molding, milling, machining or other suitable process. However, in other embodiments, the handle 210 and head 230 may be formed as separate components which are operably connected at a later stage of the manufacturing process by any suitable technique known in the art, including without limitation thermal or ultrasonic welding, a tight-fit assembly, a coupling sleeve, adhesion, or fasteners. Whether the head 230 and handle 210 are of a unitary or multi-piece construction (including connection techniques) is not limiting of the present invention, unless specifically stated. In some embodiment of the invention, the head 230 may be detachable (and replaceable) from the handle 210 using techniques well-known in the art.

The head 230 generally comprises a front surface 231, a rear surface 232 and a peripheral surface 233. The front surface 231 and the rear surface 232 of the head 230 can take on a wide variety of shapes and contours, none of which are limiting of the present invention. For example, the front and rear surfaces 231, 232 can be planar, contoured or combinations thereof. Moreover, if desired, the rear surface 232 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 230 is normally widened relative to the neck 220 of the handle 210, it could in some constructions simply be a continuous extension or narrowing of the handle 210.

The front surface 231 comprises a collection of oral cleaning elements such as tooth engaging elements 235 extending therefrom for cleaning and/or polishing contact with an oral surface and/or interdental spaces. While the collection of tooth engaging elements 235 is preferably suited for brushing teeth, the collection of cleaning elements 235 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material preferably has a hardness property in the range of A8 to A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 235 of the present invention can be connected to the head 120 in any manner known in the art. For example, staples/anchors, in-mold tufting (IFT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 200 and the dispenser 300 are non-unitary separate structures that are specially designed to be non-fixedly secured together when in an assembled state (referred to herein as a storage state) and completely separated from one another when in a disassembled state (referred to herein as an application state). The toothbrush 200 and the dispenser 300 are illustrated in the storage state in FIGS. 1 and 2 and in the application state in FIG. 3. The dispenser 300 can be slidably manipulated and moved between the storage state (FIGS. 1 and 2) in which the dispenser is docked in toothbrush handle portion 210 and the application state (FIG. 3) in which the dispenser is removed from handle portion 210 by the user as desired. The dispenser docking system for nesting and disengagement of dispenser 300, and the relevant structural elements of the toothbrush 200 and dispenser 300 comprising the docking system, will now be described in greater detail.

Figure 4:
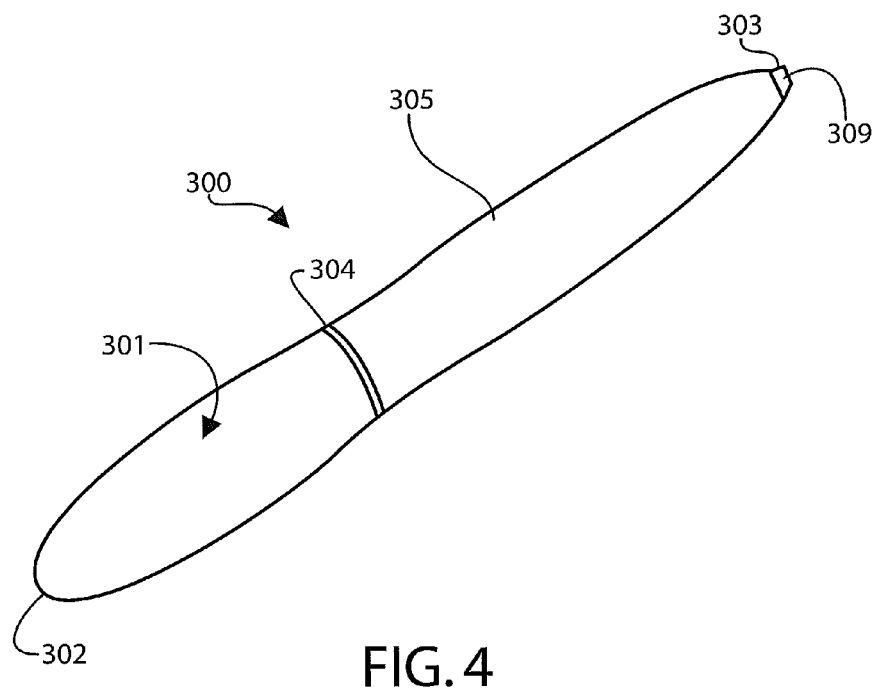
FIG. 4 is a perspective view of the dispenser of the oral care system of FIG. 1.
Figure 5:
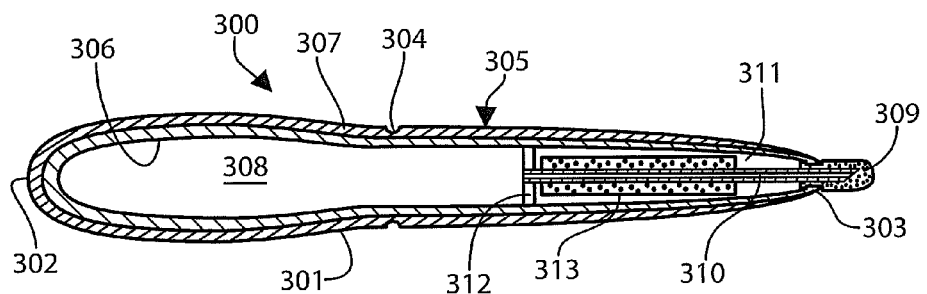
FIG. 5 is a longitudinal cross-sectional view of the dispenser of FIG. 4.

Referring now to FIGS. 4 and 5, the dispenser 300 is schematically illustrated. The dispenser 300 is an elongated tubular pen-like structure. The dispenser 300 has a housing 301 that extends between a gripping end 302 (which can be conceptually considered as the proximal end) and a dispensing end 303 (which can be conceptually considered as the distal end). An annular groove 304 is formed into the outside surface 305 of the housing 301. While the groove 304 is located near a middle point along the length of the housing 301, the groove 304 can be located on the housing 301 at any position desired. Moreover, while the groove 304 is illustrated as a concisely defined channel, in other embodiment the groove can be formed by a gradually sloping curvature and/or contour of the housing 301.

The housing 301 comprises an inner layer 306 and an outer layer 307. The inner layer 306 is preferably constructed of a material that is sufficiently rigid to provide the necessary structural integrity for the dispenser 300. For example, the inner layer can be made out of a moldable hard plastic. Moldable thermoplastics are preferred. Suitable plastics include polymers and copolymers of ethylene, propylene, butadiene, vinyl compounds and polyesters such as polyethylene terephthalate. The chosen plastic(s), however, must be compatible with the oral care agent that is to be stored within the dispenser 300 and should not be corroded or degraded by the oral care agents.

The outer layer 307 is preferably made of a soft resilient material, such as an elastomeric material. Suitable elastomeric materials include thermoplastic elastomers (TPE) or other similar materials used in oral care products. The elastomeric material of the outer layer 307 may have a hardness durometer measurement ranging between A13 to A50 Shore hardness, although materials outside this range may be used. A preferred range of the hardness durometer rating is between A25 to A40 Shore hardness. While an over-molding construction is preferred for the outer layer 307, a suitable deformable thermoplastic material, such as TPE, may be formed in a thin layer and attached to inner layer 306 with an appropriate adhesive or by other means. It should be noted, however, that in some embodiments of the invention, the housing 301 may be constructed of a single layer of material.

Figure 7A:
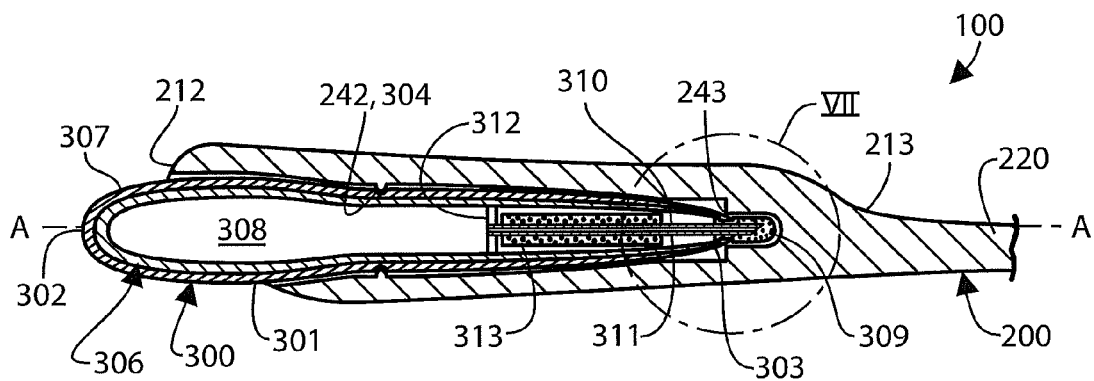
FIG. 7A is a longitudinal cross-sectional view of the oral care system of FIG. 1 in the storage state.

Referring to FIGS. 5 and 7A, the housing 301 forms an internal chamber which defines a reservoir 308 for holding the desired oral care material or product, which can be any active or inactive oral care agent. The oral care agent and/or its carrier may be in any form such as a solid or a flowable material including without limitation viscous pastes/gels or less viscous liquid compositions. Preferably, the oral care agent is a flowable material in preferred embodiments. Any suitable oral care agent can be used in the present invention. For example, the oral care agent includes whitening agents, including without limitation, peroxide containing tooth whitening compositions. Suitable peroxide containing tooth whitening compositions are disclosed in U.S. patent Ser. No. 11/403,372, filed Apr. 13, 2006, to the present assignee, the entirety of which is hereby incorporated by reference. While a tooth whitening agent is one of the preferred active agents in the present invention, any other suitable other care agents can be used with embodiments of the present invention and, thus, stored within the reservoir 308. Contemplated oral care agents can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The oral care agent in one embodiment is preferably free of (i.e., is not) toothpaste. Instead, the active agent is intended to provide supplemental oral care benefits in addition to merely brushing one's teeth. Other suitable oral care agents could include lip balm or other materials that are typically available in a semi-solid state.

The reservoir 308 is fluidly coupled to an applicator 309 which protrudes from the dispensing end 303 of the housing 301 by a delivery channel 310. The delivery channel 310 delivers the oral care agent from the reservoir 308 to the applicator 309. Of course, in some embodiments, a delivery channel may not be necessary or may merely be an extension of the reservoir or a space connecting the reservoir and the applicator (or an opening in the dispensing end). The user then presses and/or rubs the applicator 309 against his/her teeth to apply the oral care agent to his/her teeth, preferably after brushing. The application process is much like using a standard pen and/or marker.

The applicator 309 may be constructed of bristles, a porous or sponge material, or a fibrillated material. Suitable bristles include any common bristle material such as nylon or PBT. The sponge-like materials can be of any common foam material such as urethane foams. The fibrillated surfaces can be comprised of various thermoplastics. In the use of a bristles, the delivery channel 310 will deliver the composition to near the ends of the bristles. Usually there will be a single delivery channel. For sponge and fibrillated surfaces there usually will be plurality of smaller diameter channels so as to more uniformly distribute the composition onto the user's teeth. In one embodiment, the fibrillated material will have an essentially planar surface that has a plurality of protruding fibrils up to about 3 millimeter in length. Such a fibrillated surface provides a mini-brush surface. The invention, however, is not so limited and the applicator 309 can be any type of surface and/or configuration that can apply a viscous substance onto the hard surface of teeth including merely an uncovered opening/orifice.

The delivery channel 310 can be a suitable sized tubular conduit having a hollow passageway or it can be constructed of a porous material. The mechanism of delivery of the active agent from the reservoir 308 to the applicator 309 (or an orifice in the dispensing end) can be strictly by capillary action, a mechanical or chemical pumping action, compression/squeezing of the dispenser 300, gravity and/or combinations thereof. In one embodiment, at least a portion of the housing 301 can be constructed to be transversely deformable so that the user can squeeze the dispenser 300, thereby increasing the pressure inside reservoir 308 and forcing the oral care agent outwards from the reservoir 308 through the applicator 309. In such an embodiment, a one-way valve may be built into the dispenser to allow air back into the reservoir so that the dispenser housing 301 resumes its uncompressed/un-deformed state after use. In other embodiments, a piston-like mechanism can be used to the whitening agent from the reservoir 308 to the applicator 309. Of course, other mechanisms and actions can be used to achieve the dispensing goal.

In the illustrated embodiment of the dispenser 300, an overflow chamber 311 is created near the dispensing end 303 by the addition of a transverse wall 312. The transverse wall 312 separates and substantially seals the reservoir 308 from the overflow chamber 311. The delivery channel 310 extends through the transverse wall 312 and through the overflow chamber 311, thereby fluidly coupling the reservoir 308 to the applicator 309. A porous material, which is in the form of a sleeve 313 can be positioned within the overflow chamber 311. The overflow chamber 311 can minimize excessive amounts of the oral care agent from reaching the applicator 309 or leaking from the dispenser 300. The overflow chamber 311 will not be needed in all embodiments of the dispenser, depending on the delivery mechanism used.

The details of the dispenser 300 described above are not to be considered limiting of the present invention unless specifically recited in the claims. It is to be understood that the structural details of the dispenser body and its fluid delivery system can vary greatly.

However, in one embodiment, in order to make the oral care system 100 user friendly for travel, the reservoir 308 and/or the volume of active agent in the reservoir may be selected so that the oral care system 100 can be taken on airplanes. Since about 2002, the volume of liquid that can be taken onto an airplane in the U.S. and other countries in a single container is limited, typically to about 3 fluid oz. The reservoir 308 and/or the volume of active agent in the reservoir 308 are selected to meet the applicable regulatory standard, which may change from country to country and/or over time. The reservoir 308 and/or volume of active agent in the reservoir 308 may be at least 8 fluid oz., or sufficient for at least two weeks of use by an average user.

Furthermore, in some embodiments of the invention, the applicator 309 may be omitted from the dispenser 300. In such an embodiment, the desired oral care material will be delivered from the reservoir 308 of the dispenser 300 via a mere orifice in the dispensing end 303. Depending on the type of oral care material being used, this orifice may act like a nozzle or port for dispensing and/or ejecting a liquid or paste oral car material to the desired oral surface. Such an arrangement is especially useful when combined with a compressible/squeezable dispenser housing. In embodiments where a semi-solid oral care material is used, such as lip balm, the orifice may merely provide a passageway from the reservoir through which the semi-solid oral care material will protrude or can be slidably extended and retracted by any suitable conventional axial or rotary extension mechanism.

Figure 6:
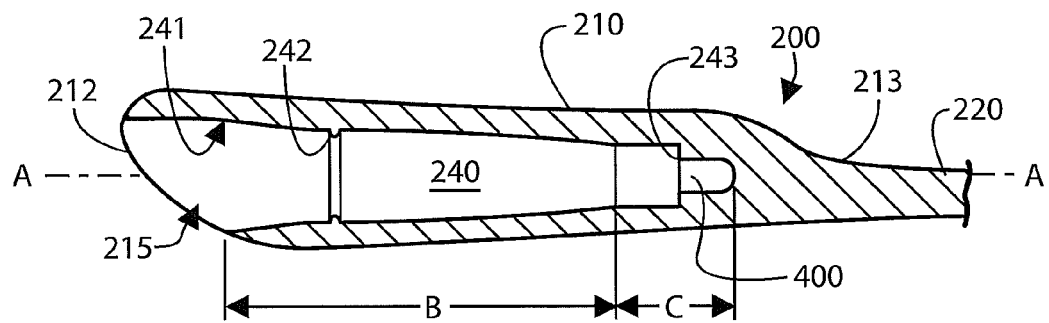
FIG. 6 is a longitudinal cross-sectional view of the handle of the toothbrush of the oral care system of FIG. 1.
Figure 7B:
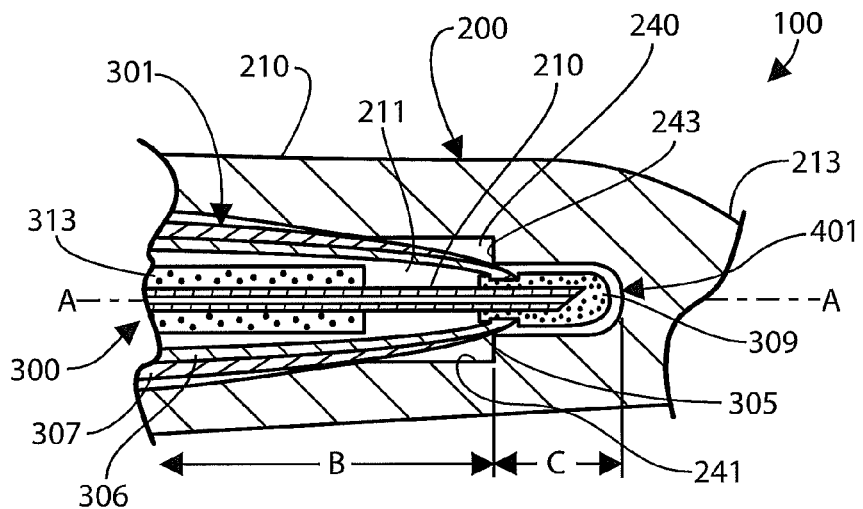
FIG. 7B is a close-up view of area VII of FIG. 7A.

Referring now to FIGS. 6, 7A, and 7B, the details of the toothbrush 200 which provide a nesting volume for the dispenser 300 in the docketed or storage state will be described. The handle 210 of the toothbrush 200 comprises an internal cavity 240 that is sized and shaped to accommodate the dispenser 300. The cavity 240 is a generally tubular cavity that extends along the longitudinal axis A-A of the handle 210 and is defined by an inner surface/wall 241. The opening 215, which is a substantially transversely oriented and located at the proximal end 212 of the handle 210 in one embodiment, provides a passageway from exterior of the toothbrush 200 to the internal cavity 240. The opening 215 is sized and shaped to allow the dispenser 300 to be slid into and out of the internal cavity 240. The size and shape of the cavity 240 generally corresponds to the size and shape of the dispenser 300 and, as described below with respect to FIG. 7A, non-fixedly and removably secures the dispenser 300 within the handle 210.

The cavity 240 comprises longitudinal section B and longitudinal section C. Section B of the cavity 240 is sized and shaped to accommodate the housing 301 of the dispenser 300 while section C of the cavity 240 is sized and shaped to accommodate the applicator 309 and distal dispensing end 303 of the dispenser 300. More specifically, section B has transverse and longitudinal cross-sectional profiles that generally correspond to the transverse and longitudinal cross-sectional profiles of the portion of the housing 301 of the dispenser 300 that nests within the cavity 240. Similarly, section C has transverse and longitudinal cross-sectional profiles that generally correspond to the transverse and longitudinal cross-sectional profiles of the applicator 309 and distal dispensing end 303 of the housing 301 of the dispenser 300 that nests within the cavity 240. Of course, the invention is not limited to such correspondence in all embodiments.

With continuing reference to FIGS. 6, 7A, and 7B, the cavity 240 has a generally tapered transverse section for a major portion of the longitudinal length of the cavity comprising sections A and B, wherein the transverse cross-section decreases as one moves forward/away from the opening 215 towards distal end 213 of handle portion 210. The tapered transverse cross-section of the cavity 240 assists with guiding and centering the dispenser 300 into proper placement and seating within the cavity 240 in the docked or storage state. The transverse cross-sectional area of section C is preferably substantially less than the transverse cross-sectional area of section B to coincide with the corresponding tapered shape of dispenser 300. As best shown in FIG. 6, in one embodiment the plane of the opening 215 is preferably angled transversely with respect to the longitudinal axis so as to further assist with the removal from and reinsertion of the dispenser into the cavity 240.

With continuing reference to FIGS. 6, 7A, and 7B, the inner wall 241 of the cavity 240 comprises an annular ridge 242 that is designed to non-fixedly mate with the annular groove 304 of the dispenser 300 when in the storage state. The annular ridge 242 and groove 304 provides a locking system for removably securing dispenser 300 in handle portion 210 of toothbrush 200. In one possible embodiment, annular ridge 242 is preferably convex shaped in cross-section and groove 304 may have a complementary concave cross section to facilitate a smooth but locking engagement between the ridge and groove (see FIGS. 6 and 7A). Of course, other mating shapes and/or features can be utilized on the dispenser 300 and wall 241 instead of a groove/ridge arrangement for removably securing dispenser 300 in handle portion 210 of toothbrush 200. Annular ridge 242 may form a transition between section B and section C of the cavity 240 as shown.

With continuing reference to FIGS. 6, 7A, and 7B, inner wall 241 of cavity 240 also further may include an annular shoulder 243 that preferably is located near distal end 213 of handle portion 210 as shown. The annular shoulder 243 provides a protruding structure that creates the smaller distal transverse cross-sectional area of section C in the form of an applicator end receptacle 400 near distal end 213 of handle portion 210. While the annular shoulder 243 is illustrated as a rectangular corner or edge, it can take on a wide variety of shapes and cross-sectional profiles or contours, including an angled edge, a curved radius or arcuate edge, or others. The annular shoulder 243 is configured and adapted to mutually engage the distal dispensing end 303 of dispenser 300 when inserted fully into cavity 240. This provides a stopper for the dispensing end 303 of the housing 301 of the dispenser 300 so as to prevent over-insertion and contact between the forward-most transverse/vertical distal end wall 401 of inner wall 241 of the cavity and the free end of applicator 309 that could lead to "bleeding" or leaking of the oral care agent from the dispenser into the cavity which creates a mess and loss of oral care agent. Accordingly, annular shoulder 243 preferably creates a small gap between the free end of applicator 309 and distal end wall 401 of the cavity 241 (see FIG. 7B). Receptacle 400 is further preferably configured and sized to receive applicator 309 therein and may generally conform to the shape and size of the applicator while providing a suitable circumferential gap therebetween so as to also prevent lateral engagement between the applicator and end receptacle 400 to prevent leaking. Of course, in some embodiments of the invention, the annular shoulder may be omitted wherein the cavity 241 and dispenser 300 may preferably be mutually configured so that a small gap remains between the end of applicator 309 and distal end wall 401 of the cavity when the dispenser 300 is fully seated and docked in cavity 241 of handle portion 210 of toothbrush 200. The annular shoulder 243 and its structural cooperation with the dispenser 300 will be described in greater detail below.

Referring now to FIGS. 7A and 7B concurrently, the structural cooperation between the dispenser 300 and the toothbrush 200 in the storage state will be discussed in greater detail. As illustrated, the oral care system 100 is in the storage state. When in the storage state, the dispenser 300 is slidably positioned within the cavity 240 of the handle 210 of the toothbrush 200 as illustrated. A majority of the length of the dispenser 300 is nested within the cavity 240 of the toothbrush, and most preferably at least 75% of the length of the dispenser 300 is nested within the cavity 240 of the toothbrush 200.

When in the docked or storage state, the annular groove 304 of the dispenser 300 matingly receives the annular ridge 242 of the inner wall 241 of the cavity 240, thereby non-fixedly securing the dispenser 300 in its place. The mating of the groove 304 and the ridge 242 secure the dispenser in place until the user applies sufficient force so as to overcome the mating interaction between the groove 304 and the ridge 242, thereby dislodging the dispenser 300 from the toothbrush 200 for use. The exact force required to overcome the mating engagement will be dictated by the respective size and tolerances of the groove 304 and ridge 242.

The resilient outer layer 307 of the dispenser further facilitates the non-fixed securing between the dispenser 300 and the toothbrush 200 in that the outer layer 307 is compressed by the ridge 242 and/or other portions of the inner wall 241. Furthermore, the compression of the resilient outer layer 307 increases the amount of force needed to overcome the frictional contact between the inner wall 241 and the outer surface 305 of the housing 301 of the dispenser 300.

The mating between the groove 304 and the ridge 242 also performs another function in that the mating interaction forms a hermetic seal between the wall 242 and the outer surface 305 of the dispenser 300. This hermetic seal prevents water and other fluids that may compromise the integrity of the applicator 309 and/or the activity of the oral care agent from entering the cavity 240. The compression of the resilient outer layer 307 also adds to this effect. In addition to keeping water and other unwanted fluid from entering the cavity 240 when the dispenser is in the storage state, the hermetic seal also prevents the applicator from drying out during periods of non-use.

When in the docked or storage state, the annular shoulder 243 also assists in the role of maintaining the integrity of the applicator 309 and the oral care agent during periods of non-use and/or brushing with the toothbrush 200. More specifically, when in the storage state, the annular shoulder 243 contacts (and slightly compresses) the outer surface 305 of the housing 301, thereby forming a second hermetic seal and/or barrier that isolates section C of the internal cavity from the section B of the cavity 240. Thus, there are two hermetic seals protecting section C and the applicator 309 from the outside environment in the storage state. Of course, only or the other may be used. Moreover, the hermetic seals may also be formed by mere contact between the outside surface 305 of the dispenser 300 and the inner wall 241.

The hermetic seal formed by the annular shoulder may be especially helpful in preventing unwanted leaking and/or drying of the applicator 309 because of the small free volume available in section C of the cavity 240. In other embodiments, the dispenser 300 may be non-fixedly secured within the cavity 240 of the toothbrush 200 by a mere compression fit and/or frictional surface contact between the dispenser and the internal wall 241.

Figure 8:
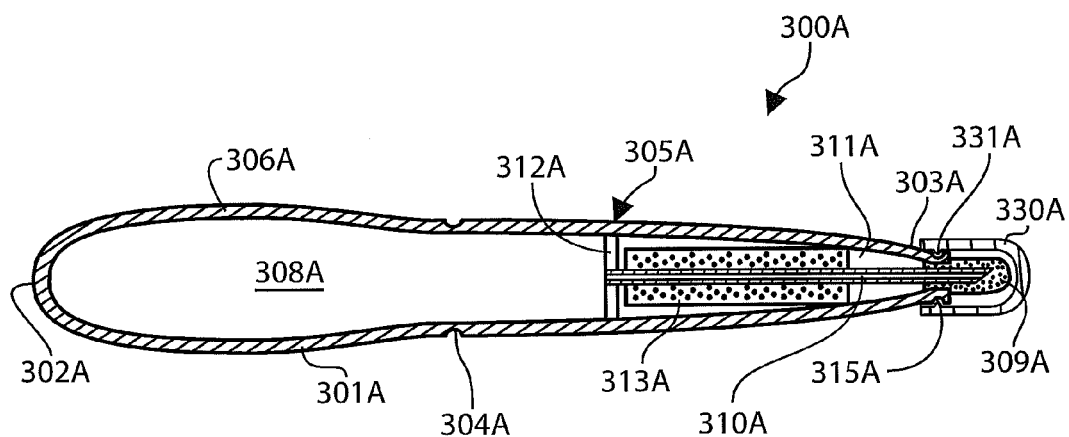
FIG. 8 is a longitudinal cross-sectional view of a dispenser according to an alternative embodiment of the invention having a cap enclosing the applicator.

Referring now to FIG. 8, an alternative embodiment of a dispenser 300A is illustrated according to the present invention. The dispenser 300A is identical to that of the dispenser 300 of FIGS. 4 and 5 with the exception that the dispensing end 303A is adapted to have a cap 330A secured thereto and is constructed of a single layer 306A of material. In order to avoid redundancy, a detailed discussion of those components of the dispenser 300A that are substantially identical to that of the dispenser 100 is omitted. However, for reference and clarity, like numbers are used to identify like parts with the exception of the alphabetical suffix "A" being added.

The dispensing end 303A of the housing 301A of the dispenser 300A includes a surface feature (in the form of an annular groove 315A) for mating with a corresponding structure (in the form of an annular ridge 331A). Mating between the annular groove 215A of the housing 301A with the annular ridge 331A of the cap 330A non-fixedly secures the cap 330A to the housing 301A, thereby enclosing the applicator 309A so as to prevent leaking and/or drying out of the active agent. While a groove/ridge mating assembly is exemplified to hold the cap 330A in place, other surface features and structures that can matingly engage and/or cooperate with one another can be used. Structures and methods of attaching a cap to a tubular body are well known in the art.

The housing 301A of the dispenser 300A is also a single layer 306A construction. The material of the single layer 306A should provide the necessary structural rigidity and be compatible with the oral care agent.

Figure 9:
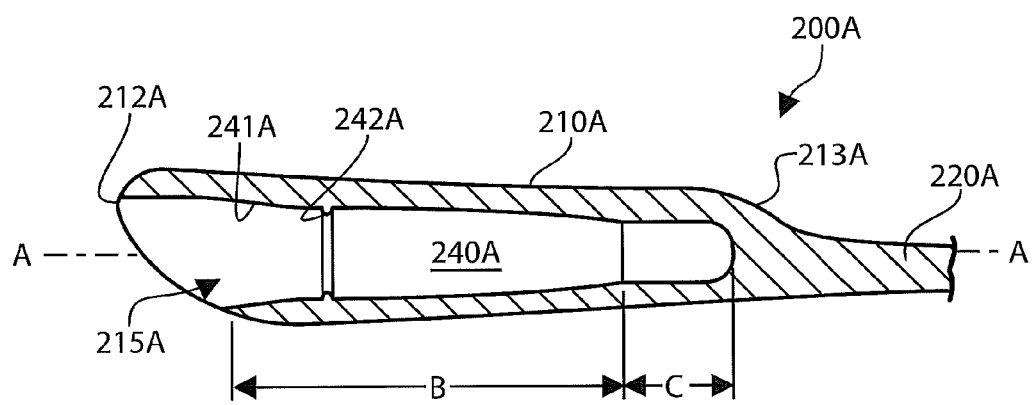
FIG. 9 is a longitudinal cross-sectional view of a toothbrush having a storage cavity designed to accommodate the dispenser (with the cap) of FIG. 8 according to the present invention.

Referring now to FIG. 9, a toothbrush 200A specifically designed to accommodate the dispenser 300A with the cap 330A remaining on is illustrated. The toothbrush 200A is identical to that of the toothbrush 200 of FIGS. 1-7B with the exception that the internal cavity 240A is shaped differently to accommodate the dispenser 300A with the cap 330A. In order to avoid redundancy, a detailed discussion of those components of the toothbrush 200A that are substantially identical to that of the toothbrush 200 is omitted. However, for reference and clarity, like numbers are used to identify like parts with the exception of the alphabetical suffix "A" being added.

Figure 10:
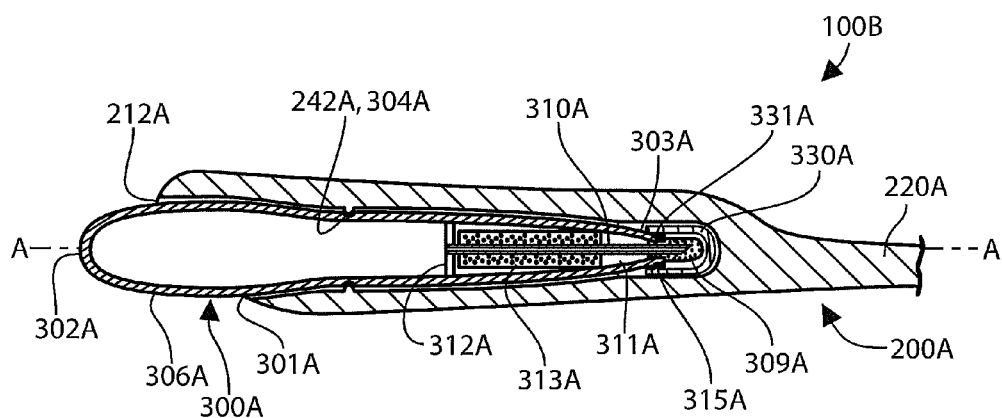
FIG. 10 is a longitudinal cross-sectional view of the toothbrush of FIG. 9 wherein the dispenser (with the cap) of FIG. 8 is non-fixedly secured within the storage cavity.

The internal cavity 240A of toothbrush 200A has a section C that is designed to accommodate the cap 330A of the dispenser 300A. Because the cavity 240A accommodates the dispenser 300 with its cap 330A attached, there is no need for a shoulder to be built into the wall 241A as the cap 330A forms a second hermetic seal for the applicator 309A. The dispenser 300A (with the cap 330A) is shown in the storage position within the toothbrush 200A in FIG. 10.

Figure 11:
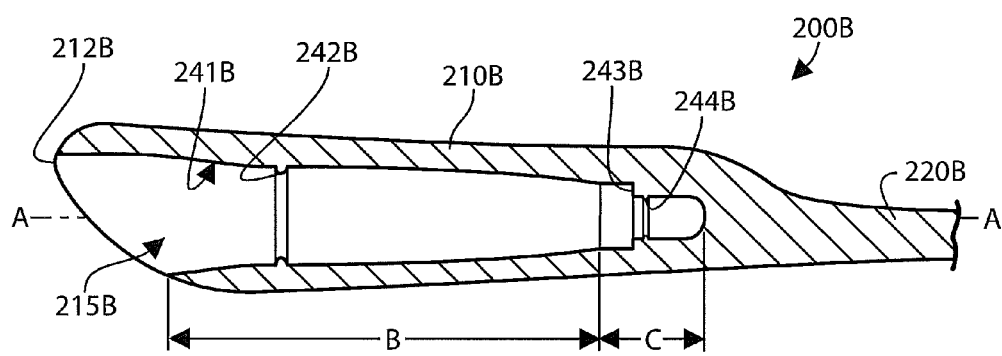
FIG. 11 is a longitudinal cross-sectional view of a toothbrush having a storage cavity designed to accommodate the dispenser of FIG. 8 (without the cap) according to the present invention.
Figure 12:
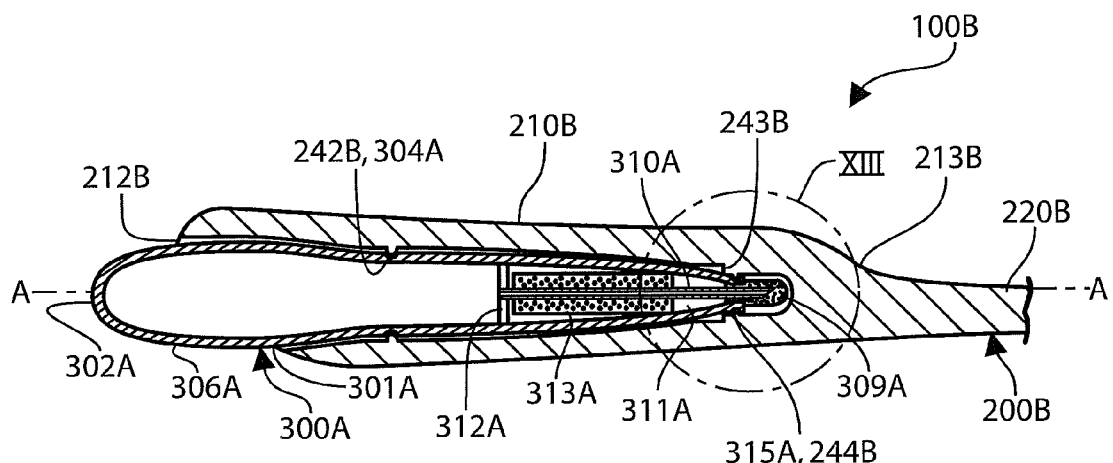
FIG. 12 is a longitudinal cross-sectional view of the toothbrush of FIG. 11 wherein the dispenser of FIG. 8 (without the cap) is non-fixedly secured within the storage cavity.
Figure 13:
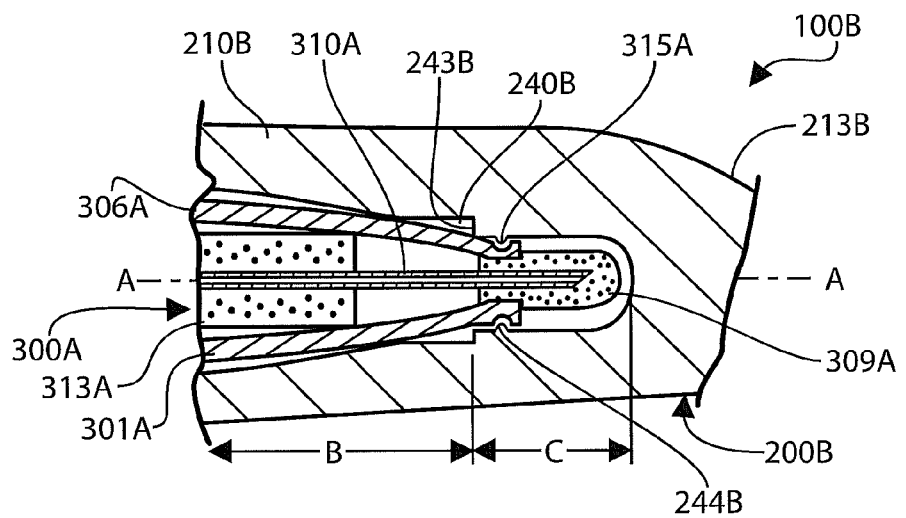
FIG. 13 is a close-up view of area XIII of FIG. 12.

Referring now to FIGS. 11-13 concurrently, a toothbrush 200B specifically designed to accommodate the dispenser 300A without the cap 330A on is illustrated. The toothbrush 200B is identical to that of the toothbrush 200 of FIGS. 1-7B with the exception that section C of the internal cavity 240B is shaped differently to accommodate the dispenser 300A without the cap 330A. In order to avoid redundancy, a detailed discussion of those components of the toothbrush 200B that are substantially identical to that of the toothbrush 200 is omitted. However, for reference and clarity, like numbers are used to identify like parts with the exception of the alphabetical suffix "B" being added.

Section C of the cavity 240 B is designed to accommodate the applicator 309A of the dispenser 300A without its cap. Of particular interest is the fact that section C of the cavity 240B is specifically designed to mate with the annular groove 315 located at the dispensing end 303A of the dispenser 300A. Specifically, the inner wall 241B further comprises an annular ridge 244B located in section C of the cavity 240B. When the dispenser 300A is in the storage state (without the cap) within the toothbrush 200B, the annular ridge 244B mates with the annular groove 315B of the dispenser 300B, thereby sealing and enclosing the applicator 309A.

Conceptually, the inner wall 240B of section C of cavity 240B is contoured to be identical to the structure of the cap 330A. Thus, even though the cap 330A is removed, the same level of protection and conservation of the applicator 309A (and the active agent) is achieved. As a result the groove 304A can be omitted if desired. The same surface feature (exemplified as the groove 315A) of the dispenser 300A can be used to: (1) secure a cap 330A to protect the applicator 309A during shipping and/or when on sale; (2) assist with non-fixedly securing the dispenser 300A within the cavity 240B in the storage state; and (3) seal and protect the applicator 309A in the storage state.

As a result of the aforementioned changeability between the cap 330A and section C of the cavity 240A, the oral care system 100B is especially suitable for sale as a kit. Replacement dispensers 300A can be sold without the need to keep of the track of the cap 330A once it is removed and used with the toothbrush 200B.

The oral care system 100 of FIGS. 1-7B can also be sold as a kit. Any kit can include at least one toothbrush 200 and one dispenser 300 holding an oral care agent. In other embodiments, a kit may include at least one toothbrush 200 and a plurality of dispensers 300; each dispenser 300 holding a different oral care agent formulation (e.g. whitening, enamel protection, anti-sensitivity, fluoride, tartar protection, etc.). The dispensers 300 may further be marked with indicia and/or color coded to identify and correspond with the particular oral care formulation contained inside. In yet further embodiments of the kit, toothbrush 200 may have a user-replaceable head 230 and the kit may include one or preferably more such heads of different types and/or configurations of tooth cleaning/engaging elements 235 and/or tongue cleaners.

Figure 14:
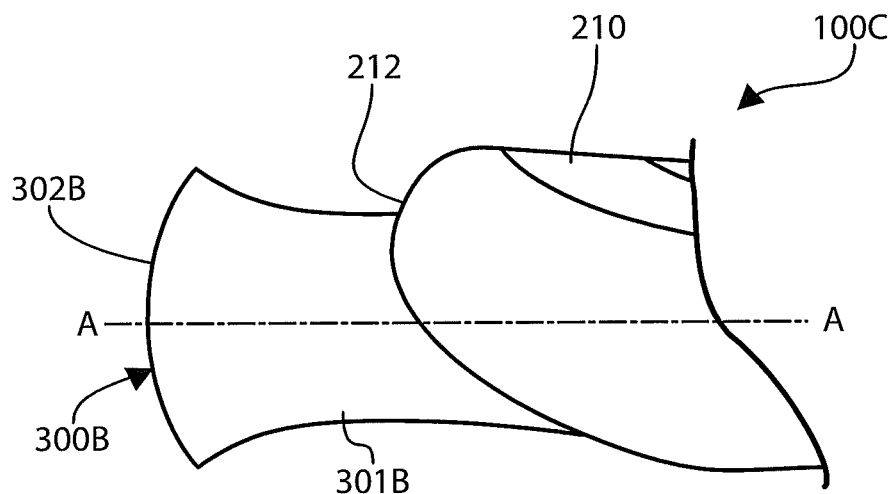
FIG. 14 is a side view of the gripping end of a dispenser protruding from the handle of the toothbrush according to one embodiment wherein the gripping end is shaped for ease of gripping.
Figure 15:
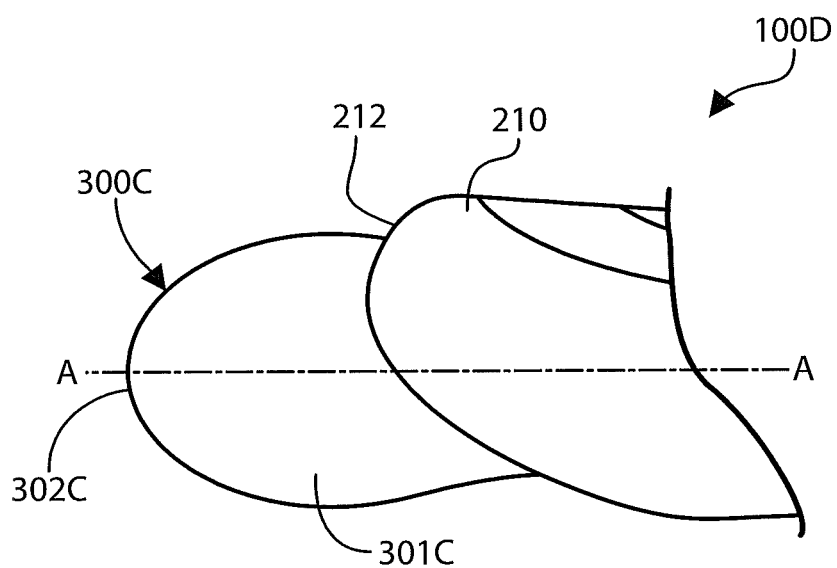
FIG. 15 is a side view of the gripping end of a dispenser protruding from the handle of the toothbrush according to another embodiment wherein the gripping end is shaped for ease of gripping.

Referring now to FIGS. 14 and 15 concurrently, oral care systems 100C and 100D are illustrated. The oral care systems 100C and 100D are identical to that of the oral care system 100 of FIGS. 1-7B with the exception that gripping ends 302B, C of the dispenser 300B, C are shaped so that a user can easily grasp the dispensers 300B, C for removal from the toothbrushes 200. Dispenser 300B has a flared end while dispenser 300C has a bulbous end.

FIGS. 16-34 show an alternative embodiment of an oral care system according to the present invention which may be an oral care system 500 in some embodiments. In this embodiment, as further described below, the toothbrush handle has a longitudinally elongated opening leading to a cavity adapted for removably receiving a dispenser therein. The opening in this alternative toothbrush handle is formed along a substantial longitudinal portion of the handle, whereas opening 215 in handle portion 210 of toothbrush 200 previously described with respect to system 100 (see, e.g. FIG. 6) is substantially located in the proximal end 212 portion of the handle and axially aligned with the longitudinal axis. Furthermore, whereas oral care agent dispenser 300 is essentially axially inserted into and removed from handle 210 and its internal cavity 240, the dispenser in this alternative oral care system embodiment 500 is at least partially laterally/transversely insertable into the handle for seating and mounting. Also, as further described herein for this alternative embodiment, the dispenser itself may form a substantial portion of the handle of the toothbrush which is gripped by the user thereby advantageously providing ready access to and convenient use of the dispenser.

Referring initially now to FIGS. 16-19, an alternative embodiment of an oral care system 500 generally includes a toothbrush 600 and a dispenser 700 removably disposed therein. The toothbrush 600 and the dispenser 700 may be generally similar to the toothbrush 200 and the dispenser 300 in structure, manufacture, and functionality to oral care system 100 and its components as already described herein, except for differences as specially noted in the description of the oral care system 500 which follows.

Figure 16:
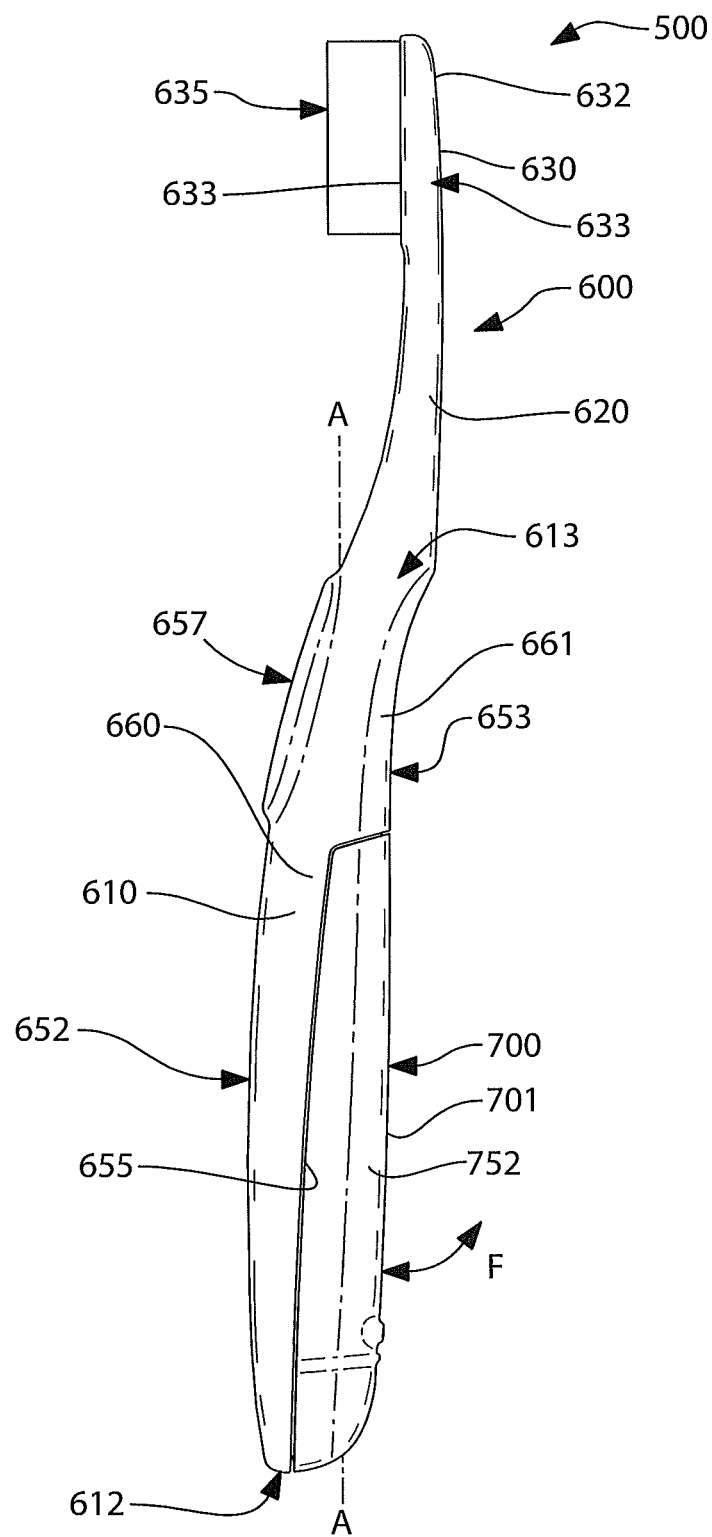
FIG. 16 is a side elevation view of a second alternative embodiment of an oral care system including a toothbrush and oral care agent dispenser according to an embodiment of the present invention.
Figure 17:
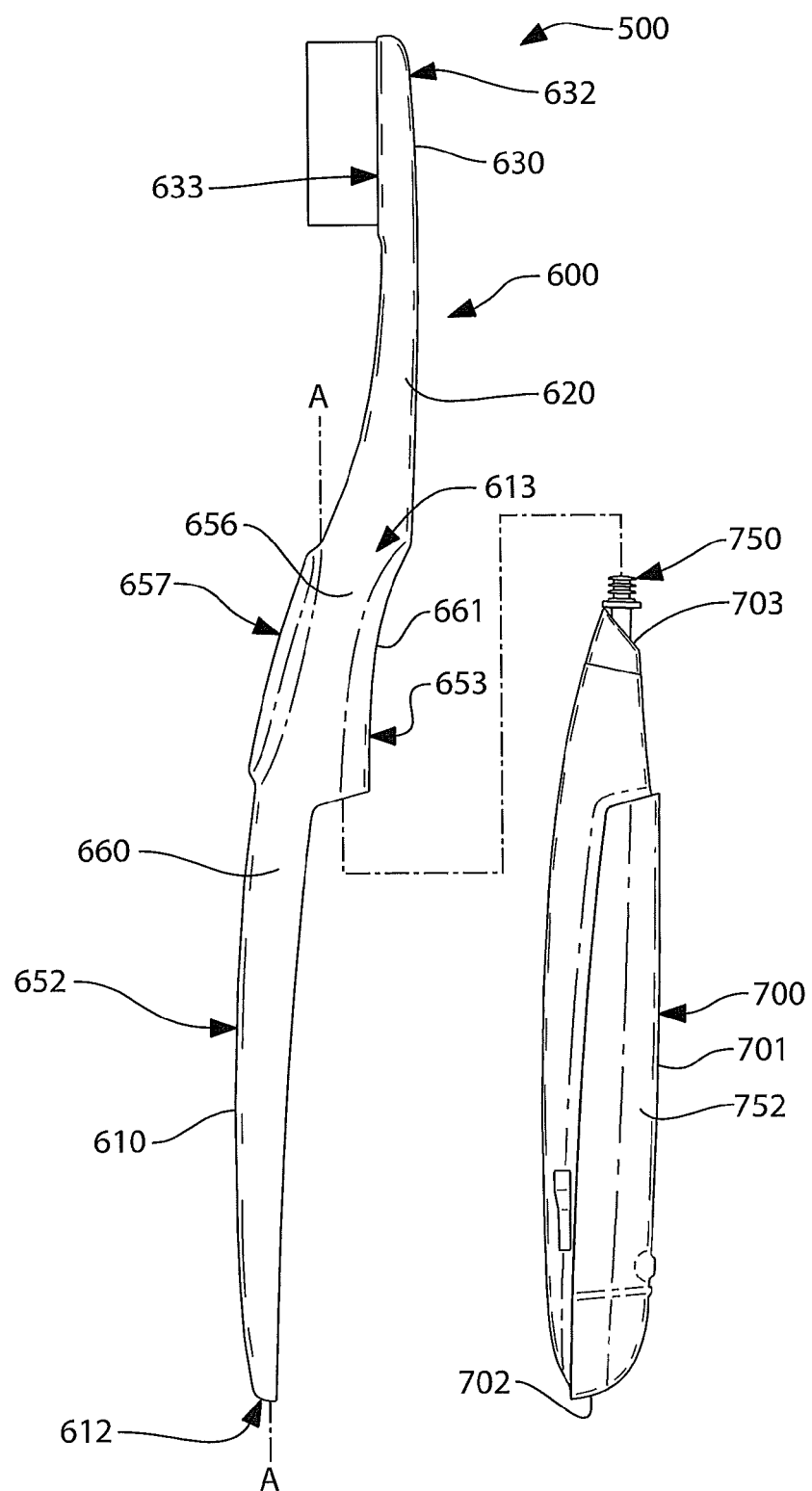
FIG. 17 is an exploded side elevation view thereof with the dispenser shown detached from the toothbrush.
Figure 18:
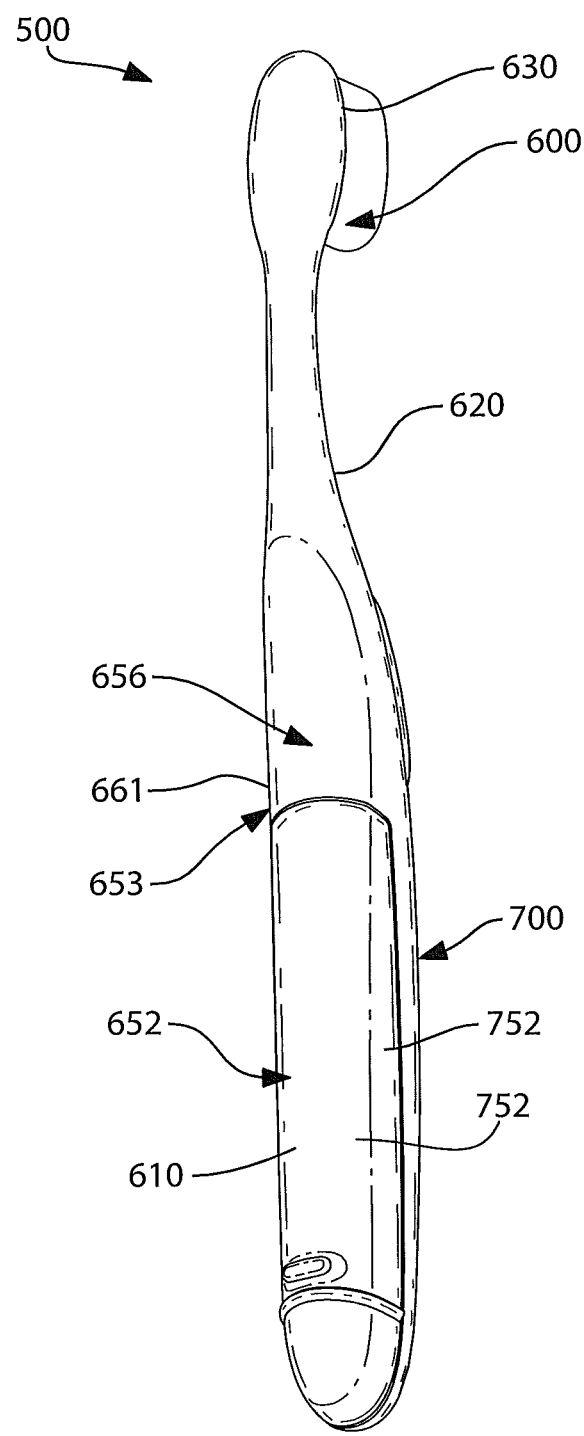
FIG. 18 is a rear perspective view of the oral care system of FIG. 16 with the dispenser mounted in the toothbrush.

The dispenser 700 is movable between a storage state shown in FIG. 16 in which the dispenser is docked or mounted in toothbrush handle 610 and an application state shown in FIG. 17 in which the dispenser 700 is dismounted or removed from the handle 610 and ready for use in an oral care regimen.

With continuing reference to FIGS. 16-20, the toothbrush 600 generally includes a handle portion 610, a neck portion 620 and a head portion 630. The handle 610 can be a single or multi-part construction. The handle 610 extends from a proximal end 612 to a distal end 613 along a longitudinal axis A-A. The handle 610 includes a top portion 660 defining a top surface or side 652, a bottom portion 661 defining a bottom surface or side 653, and pair of opposing and spaced peripheral or lateral surfaces or sides 650, 651 extending between the top and bottom sides. The top portion 660 of the handle 610 is fixedly attached to the distal end 613 portion of the handle (i.e. distal sheath portion 661 in one embodiment) and extends longitudinally rearward to the proximal end 612 of the handle 610. Accordingly, as further explained herein, the top portion 660 forms a cantilevered portion of the handle 610 that detachably engages and supports the dispenser 700. The handle 610 transitions into the neck 620 at the distal end 613 of the handle that supports toothbrush head 630 via the handle 610. While the neck 620 generally may have a smaller transverse cross-sectional area to the handle 620, the invention is not so limited.

With continuing reference to FIGS. 16-20, the toothbrush head 630, neck 620, and handle 610 of the toothbrush 600 may be formed as a single unitary structure, or in other embodiments the these parts may be formed as separate structures which are fixedly or detachably assembled together. In some embodiments, the head 630 may be removably attached to the neck 620 thereby forming a user-replaceable head that allows the user to replace heads with worn out tooth cleaning/engaging elements or interchange heads having alternate type cleaning elements. The head 630 generally comprises a front surface 631, a rear surface 632 and a lateral or peripheral surface 633. The front surface 631 comprises a plurality of oral cleaning elements such as tooth engaging elements 635 extending therefrom for contact with an oral surface and/or interdental spaces. The tooth engaging elements 635 may generally be formed from various types of cleaning elements such as those already described herein with respect to tooth engaging elements 235.

Figure 19:
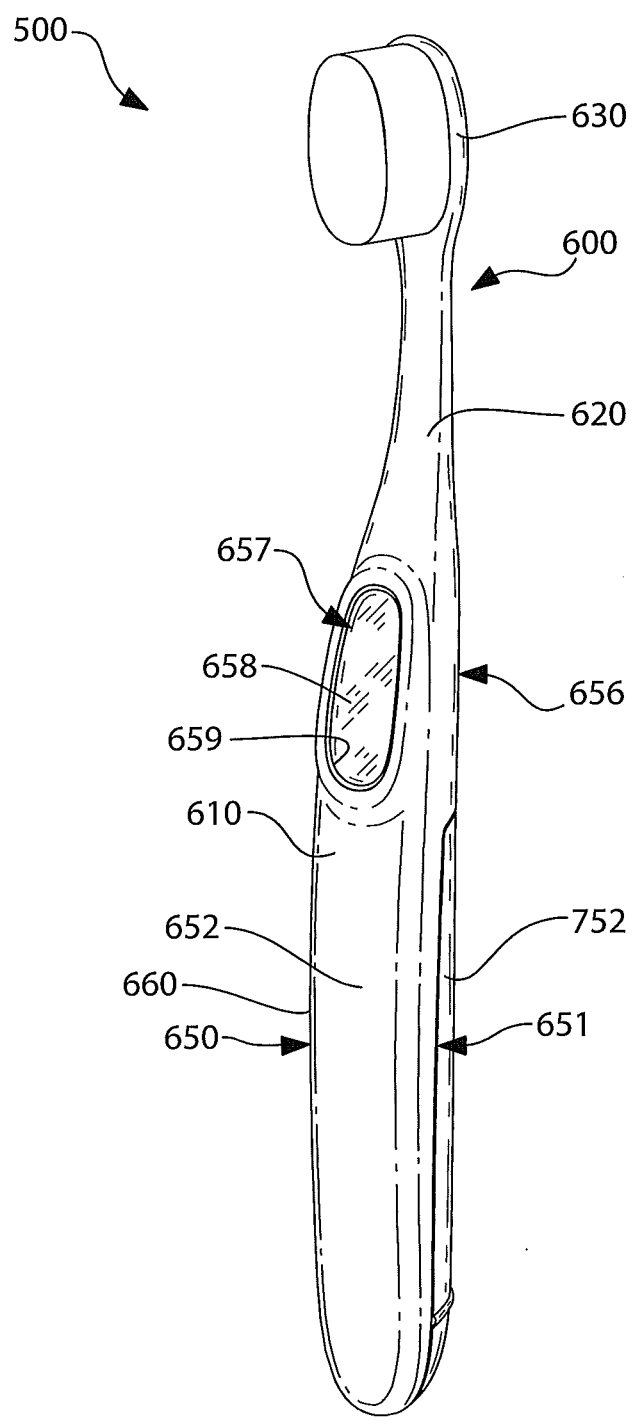
FIG. 19 is a front perspective view thereof.
Figure 20:
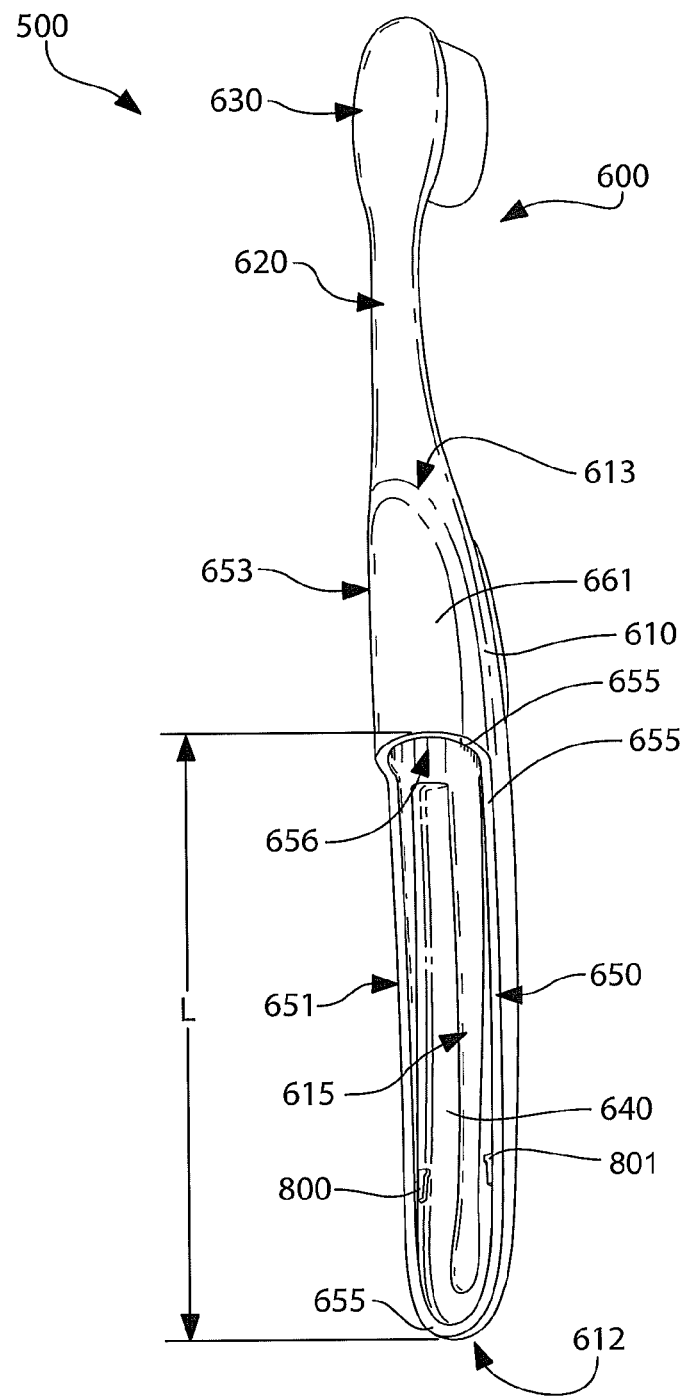
FIG. 20 is a rear perspective view thereof with the dispenser completely removed from the toothbrush.
Figure 21:
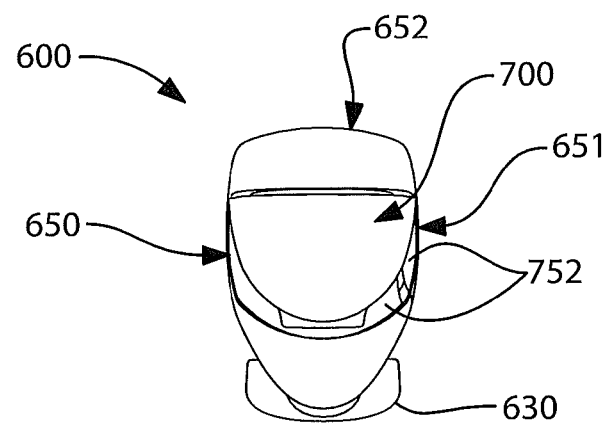
FIG. 21 is a rear end view of the oral care system of FIG. 16 with the dispenser mounted in the toothbrush.
Figure 22:
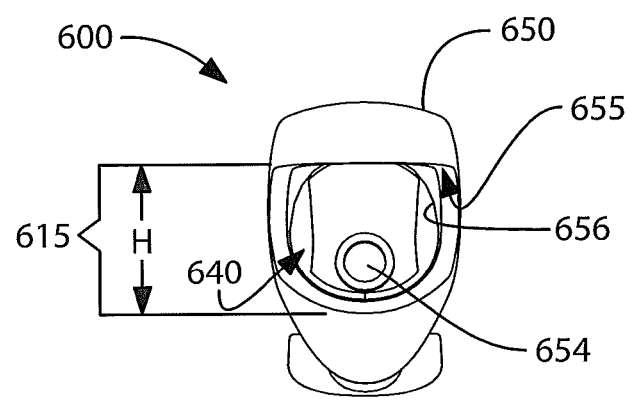
FIG. 22 is a rear end view of the oral care system of FIG. 16 with the dispenser completely removed from the toothbrush.

Referring to FIGS. 16-22, in preferred exemplary embodiments the handle 610 includes a removable portion that defines and incorporates a hand held dispenser 700 adapted to contain and dispense an oral care agent onto a target surface in an oral cavity of a user. Accordingly, a substantial portion and preferably a majority of the toothbrush handle 610 is cut away both circumferentially and longitudinally to form a largely open longitudinally extending elongated cavity 640 with access opening 615 along the lateral sides 650, 651 and bottom 653 of handle 610 for removably receiving and supporting dispenser 700. The opening 615 extends both axially and transversely to longitudinal axis A-A of toothbrush handle 610 such that the proximal end 612, lateral sides 650, 651, and bottom sides 653 of the toothbrush handle are substantially open in structure while only top side 652 is a closed structure, as best shown in FIGS. 20 and 22. When the dispenser 700 is mounted in the toothbrush handle 610, the dispenser 700 and more specifically the housing 701 comprises a substantial part of the toothbrush handle 610 in this alternative exemplary oral care system 500 as shown. In one embodiment, the housing 701 of the dispenser 700 forms substantially a majority of the lower portion or half of the toothbrush handle 610. The toothbrush handle 610 therefore has only a top portion 660 and partial side 652 in areas adjacent to the cavity 640 thereby exposing the underside of handle top side 652. The top side 652 of the handle 610 therefore provides merely a supporting core or frame for mounting dispenser 700 below the toothbrush 600 wherein the dispenser 700 substitutes for and forms a majority of the lateral sides 650, 651 and bottom side 653 of the toothbrush handle except for the distal most portion of the handle near the transition to neck portion 620. Advantageously, in contrast to embodiment shown in FIGS. 1-3, the maximum transverse cross-sectional size or diameter of housing 701 of dispenser 700 is not restricted by the transverse size or diameter of the toothbrush handle unlike handle 210 (see FIGS. 1-3 and 7A) which must be sized to accommodate a substantial portion of dispenser 300 therein as shown. In certain instances where desirable, this allows the size of dispenser 700 and associated volumetric capacity of reservoir 708 to be made as large as possible being limited primarily by only the intended overall size selected for the toothbrush 600 which will fit comfortably in the hand of the user.

Figure 31:
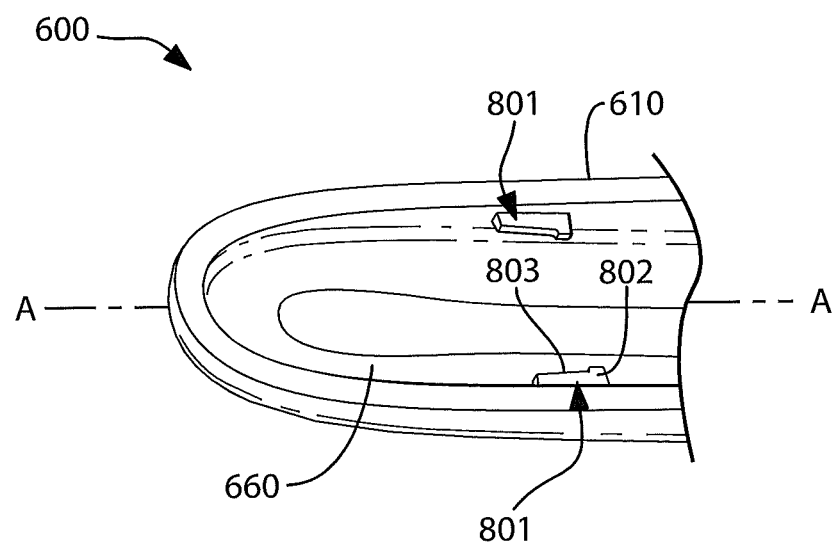
FIG. 31 is an enlarged perspective view of the rear or proximal end of the top portion of the toothbrush handle showing mounting tabs disposed thereon.
Figure 34:
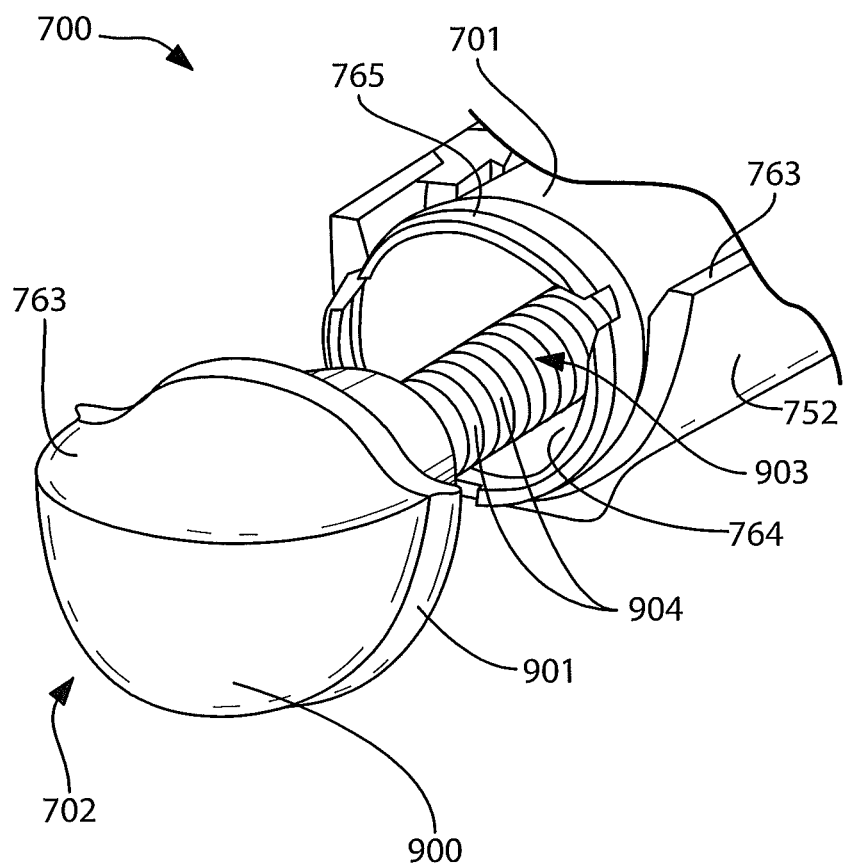
FIG. 34 is an enlarged perspective view of the rear or proximal end of the dispenser housing showing an end cap partially removed from the dispenser.

Referring primarily to FIGS. 17, 20, and 31, the toothbrush handle 610 and more particularly the top side 652 defines peripheral lateral, rear, and front mounting edges 655 which are configured and sized to mate with and engage corresponding peripheral mounting edges 763 on the dispenser housing 701 best shown in FIGS. 23-24 and 34 when the dispenser is attached to the toothbrush 600. Preferably, the edges 655 and 763 of the handle 610 and the dispenser housing 701 respectively mutually align to form a relatively uniform combined circumferential surface when joined to maintain a smooth transition between the handle 610 and the dispenser housing 701 for user comfort purposes. In some embodiments, all or part of the peripheral mounting edges 763 on the dispenser 700 may be formed on resilient soft grip 753 further described herein elsewhere. The bottom surface 753 of the dispenser 700 is also preferably contoured to smoothly transition into mating corresponding surface 653 of handle 610.

Referring now to FIGS. 17, 20, 22, and 28, exemplary embodiments of cavity 640 with access opening 615 in toothbrush handle 610 have an axial length L (FIG. 20) that preferably extends for at least half the axial length of the handle 610 measured between the distal end 613 and the proximal end 612, and more preferably for a majority of the length of the handle to maximize the volumetric storage capacity of the reservoir 708 of the dispenser 700 and to facilitate gripping the dispenser. In preferred exemplary embodiments, the opening 615 and corresponding cavity 640 extends for approximately more than half of the height H and circumference of the handle 610 as shown in FIG. 22.

Figure 28:
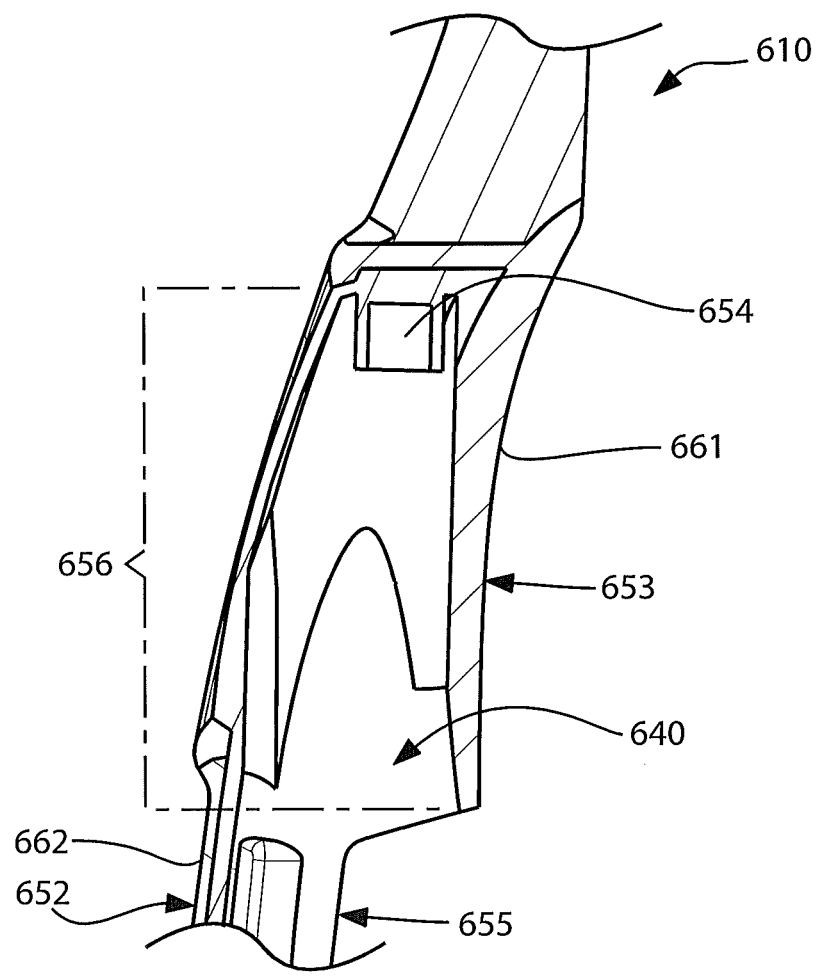
FIG. 28 is an enlarged partial side cross-sectional view of the distal end sheath portion of the toothbrush handle with the dispenser removed.

The forward most portion of the cavity 640 is preferably circumferentially enclosed by the distal end 613 of the toothbrush handle 610 as best shown in FIGS. 20, 22, and 28 to form a generally tubular sheath portion 656 configured and adapted for receiving the distal dispensing end 703 and the applicator 709 of the dispenser 700 therein. This fully enclosed sheath portion 656 facilitates secure docking of the dispenser 700 in the handle 610 and protects the applicator 709 from damage when the dispenser is in the docked or storage state affixed to toothbrush 600. The distal or front end of the sheath portion 656 is closed while the rear end of the sheath portion is open to receive the distal dispenser end 703 of dispenser therein. In some embodiments, a socket 654 may be provided at the forward-most end of the sheath portion 656 in the cavity 640 that is configured and adapted for receiving an axially protruding plug 750 disposed in the applicator 709 (see FIG. 29) to further assist with securing the distal dispensing end 703.

Figure 29:
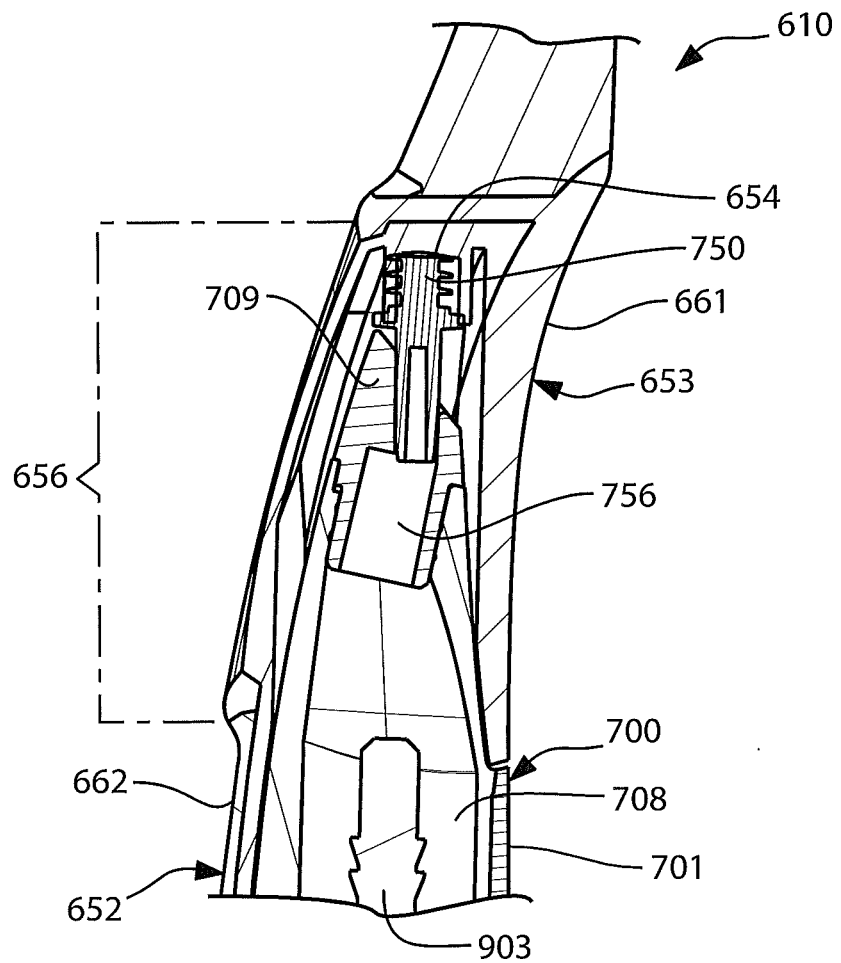
FIG. 29 is an enlarged partial side cross-sectional view thereof with the dispenser mounted in the sheath portion.
Figure 30:
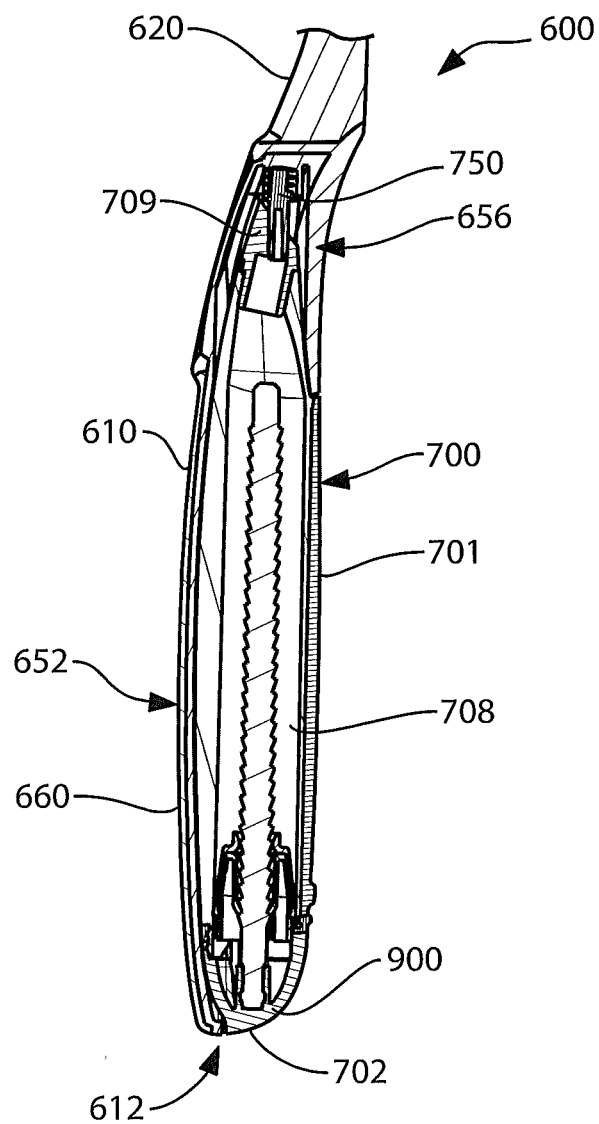
FIG. 30 is a full side cross-sectional view of the handle portion of the toothbrush with the dispenser mounted inside.
Figure 32:
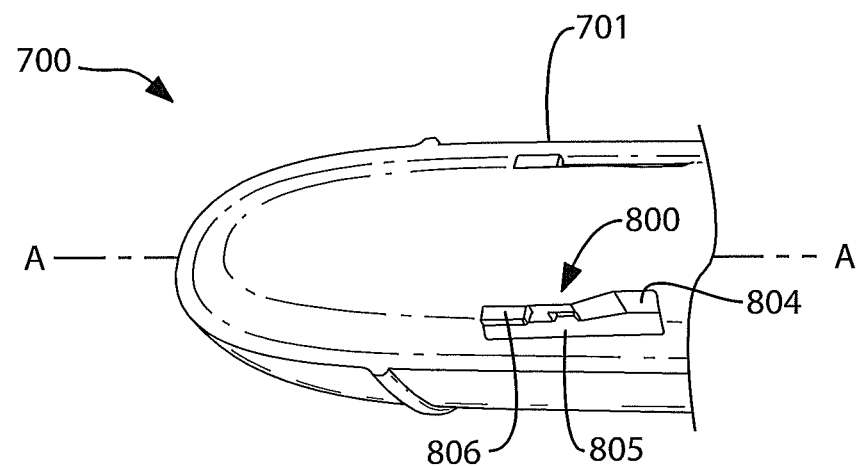
FIG. 32 is an enlarged perspective view of the rear or proximal end of the dispenser showing mounting recesses and locking lugs disposed therein.
Figure 33:
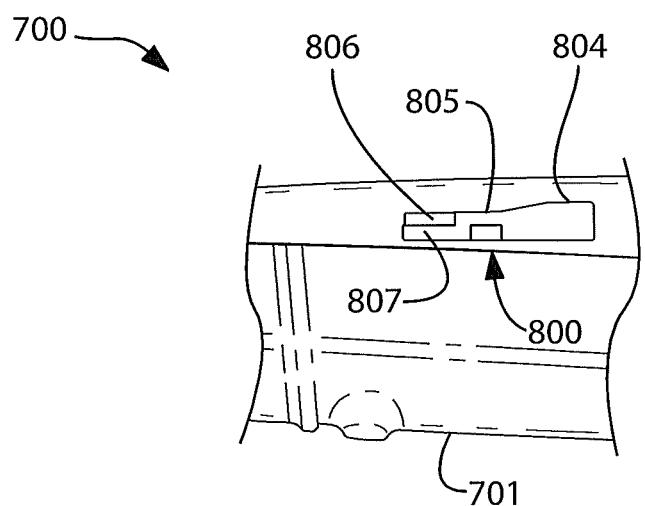
FIG. 33 is an enlarged side elevation view of the rear or proximal end of the dispenser showing the mounting recess and locking lug.

The rear portion of the dispenser 700 is detachably secured to toothbrush handle 610 via a locking mechanism disposed towards proximal end 612 of the handle. Referring to FIGS. 20, 23, 24, and 31-33, the dispenser locking mechanism 800 may be comprised of a cooperating tab and recess locking arrangement in one exemplary embodiment. The dispenser housing 701 includes a pair of laterally/transversely spaced apart mounting recesses 800 which are configured and adapted to receive a pair of laterally spaced apart mounting tabs 801 disposed on toothbrush handle 610. In one embodiment, the mounting tabs 801 are disposed on the underside of top side 652 of toothbrush housing 610 and project inwards towards longitudinal axis A-A and includes a forward enlarged section 802 and a rearward narrower section 803, as best shown in FIG. 31. The mounting recess 800 correspondingly includes a forward enlarged section 804 and a rearward narrower section 805, as best shown in FIGS. 32 and 33. The locking recess 800 further includes a locking lug 806 disposed in rearward section 805 which protrudes laterally/transversely outwards from dispenser 700. When the dispenser 700 is mounted to toothbrush handle 610, enlarged section 802 of mounting tab 801 becomes positioned in and engages corresponding enlarged section 804 of mounting recess 800 and narrower section 803 of mounting tab 801 becomes positioned in and engages the corresponding narrower section 805 of mounting recess 800. The locking lug 806 of the mounting recess frictionally engages a rear portion of the narrower section 803 of the mounting tab 801 to removably but securely attach the dispenser 700 to the toothbrush handle 610 via a characteristic "clicking" action. Since the upper side 652 of the toothbrush handle 610 adjacent the cavity 640 is preferably relatively thin in thickness to be at least partially resilient to a degree, the toothbrush handle is able to flex laterally/transversely to the longitudinal axis A-A in response to the dispenser 700 being inserted therein when the mounting tabs 801 engage the mounting recesses 800. The enlarged sections 802 of the mounting tabs 801 will tend to engage the dispenser housing first before narrower sections 803. The sections 803 are received in locking portion 807 of the recess 800 beneath the locking lugs 806 and they spring (or click) back inwards into place to complete the mounting. FIGS. 29 and 30 are cross-sectional views showing dispenser 700 fully seated or mounted in toothbrush handle 610.

The dispenser 700 will now be further described. FIGS. 23-26 show various views of the alternative dispenser 700 with FIG. 26 being a longitudinal cross-sectional view of the dispenser 700. In one embodiment, the dispenser 700 is an elongated and generally tubular pen-like structure that may be similar to the dispenser 300 already described herein (see FIGS. 5, 7A, and 7B) with respect to functionality and general construction. Some features of the dispenser 700, including the attachment mechanism for detachable mounting to handle 610, configuration, and other features, however, have been modified as will now be further described.

Figure 26:
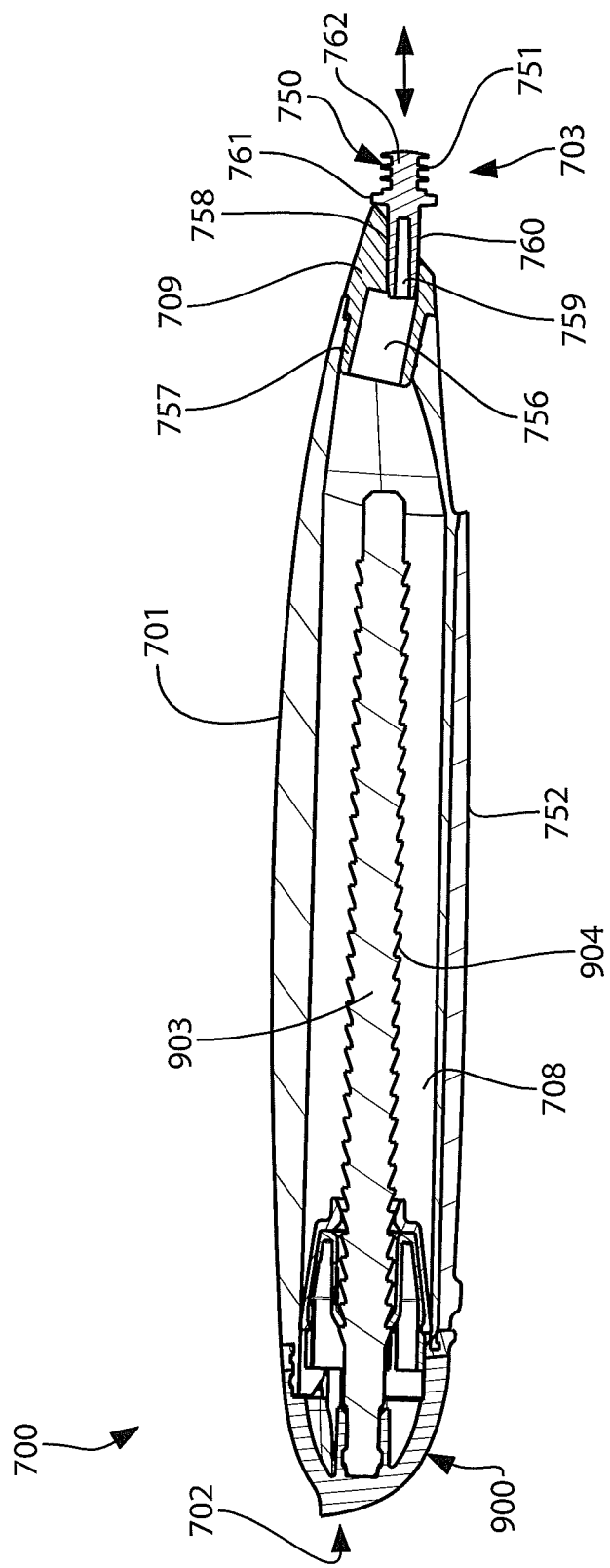
FIG. 26 is a side cross-sectional view thereof.

With continuing reference to FIGS. 23-26, the dispenser 700 includes a housing 701 that extends between a proximal end 702 and a distal dispensing end 703. As already noted herein, the housing 701 may be considered to form essentially a removable portion of the toothbrush handle 610. In some embodiments, the housing 701 may comprise inner and outer layers similarly to inner layer 306 and outer layer 307 of housing 301 shown in FIG. 5. Alternatively, in the embodiment as best shown in FIG. 26, the housing 701 has a relatively single layer shell construction formed of a preferably rigid material which may be a relatively rigid hard plastic/polymer such as a thermoplastic similar to materials already described herein with respect to the inner layer 306 of the housing 301. This provides structural rigidity to the dispenser 700. In some embodiments, at least part of housing 701 may include resiliently deformable flexible portions to allow the user to squeeze and pressurize the contents of the dispenser for delivering the active oral care agent.

Optionally, in some embodiments, at least a portion of external side of housing 701 may include a soft non-slip resilient grip 752 formed of a material such as an elastomer (e.g. as already described herein with respect to outer layer 307 of housing 301) to provide a slip resistant and comfortable gripping surface for the user. Since in this alternative oral care system 500 embodiment, the dispenser 700 substitutes for and forms a substantial functional part of the toothbrush handle 610, the resilient grip 752 in some embodiments preferably covers at least a portion of, and more preferably a majority of the exposed portions of the dispenser 700 when mounted in the handle 710. This facilitates removal and reinsertion of the dispenser 700 in the toothbrush handle 610 by the user allowing the dispenser 700 to be easily grasped, especially with wet hands after brushing. In at least one embodiment, the grip 752 may cover a majority of the lower half of the dispenser 700 and the housing 701 including the bottom surface or side 753 and portions of lateral surfaces or sides 754, 755 of the housing (see, e.g. FIGS. 21, 23-26, and 34). The grip 752 need not cover the top surface or side 766 or distal dispenser end 703 of the dispenser as these portions will be nested inside the toothbrush handle 610 when the dispenser is seated in the handle. The resilient grip 752 may be attached to the housing 701 by any suitable conventional means used in the art and already described herein, including without limitation co-molding and adhesives.

With continuing reference to FIGS. 23-26, the housing 701 forms an internal chamber which defines a reservoir 708 for holding the desired oral care agent. The oral care agents that can be used have already been described herein in detail. The reservoir 708 is fluidly coupled to an applicator 709 which protrudes forward from the dispensing end 703 of the housing 701. In this embodiment of the dispenser 700, equivalents of a delivery channel 310 and an overflow chamber 311 (see, e.g., FIG. 4 and description herein) are omitted. Instead, the oral care agent containing fluid is in direct contact with the applicator 709 as best shown in FIGS. 26 and 29. The applicator 709 may include an internal flow conduit 756 which fluidly communicates with reservoir 708 to facilitate uniform wetting of the applicator with the oral care agent.

Referring to FIGS. 23-26 and 29, the applicator 709 may be constructed of bristles, a porous or sponge material, or a fibrillated material similar to the applicator 309 already described herein. The applicator 709 includes a stem portion 757 in one embodiment which is received in and frictionally engages the distal dispensing end 703 to retain the applicator in housing 701. The applicator 709 further includes a plug 750 which is received and removably retained in the applicator. In one embodiment, the plug 750 may be formed of polypropylene or an elastomeric material, examples of which are already described herein. In one possible exemplary embodiment, the plug 750 includes a forward head 762 and an adjoining rearward extending stem 760 which is removably received in an axial orifice such as passageway 758 formed in forward end of the applicator 709.

Passageway 758 fluidly communicates with flow conduit 756 of applicator 709 and provides an orifice for dispensing the flowable oral care agent or other oral care agent from the dispenser 700. Preferably, the passageway 758 has a smaller cross-sectional internal diameter and flow area than adjoining flow conduit 756 to restrict and regulate the flow of oral care agent from the dispenser 700. Based on the viscosity of the flowable oral care agent delivered by the dispenser, one skilled in the art can readily determine an appropriate internal diameter (i.e. orifice size) for the passageway 758 to establish a desired dispensing flow rate of the product to a user. In contrast to the porous type applicator 309 shown in FIG. 4 which does not have an open flow delivery conduit or pathway extending completely through the applicator to the outside, the orifice dispensing system used in applicator 709 is advantageously better suited for dispensing more viscous oral care agents or products such as gels and pastes.

With continuing reference to FIGS. 23-26 and 29, the plug 750 including head 762 and stem 760 may be generally cylindrical in shape. The plug 750 may further include an annular flange 761 to prevent over insertion of the plug into the passageway 758 (see FIGS. 26 and 29).

With additional reference now to FIGS. 28 and 29, the removable plug 750 may further include a plurality of radially-protruding flexible annular ribs 751 which serve several functions. The ribs 751 are configured and adapted to elastically deform and frictionally engage a complementary configured cylindrical socket 654 disposed internally in the toothbrush handle 610 near the distal end 613 at the forward-most portion of internal cavity 640. The ribs 751 detachably secure the distal dispensing end 703 in toothbrush handle 701. The plug 750 further provides additional benefits, including preventing spilling of oral care agent while filling dispenser 700 during manufacturing, reducing the chance for oral care agent to leak after the manufacturing phase, and keeping the exposed applicator 709 tip clean in between uses by the user.

Figure 27:
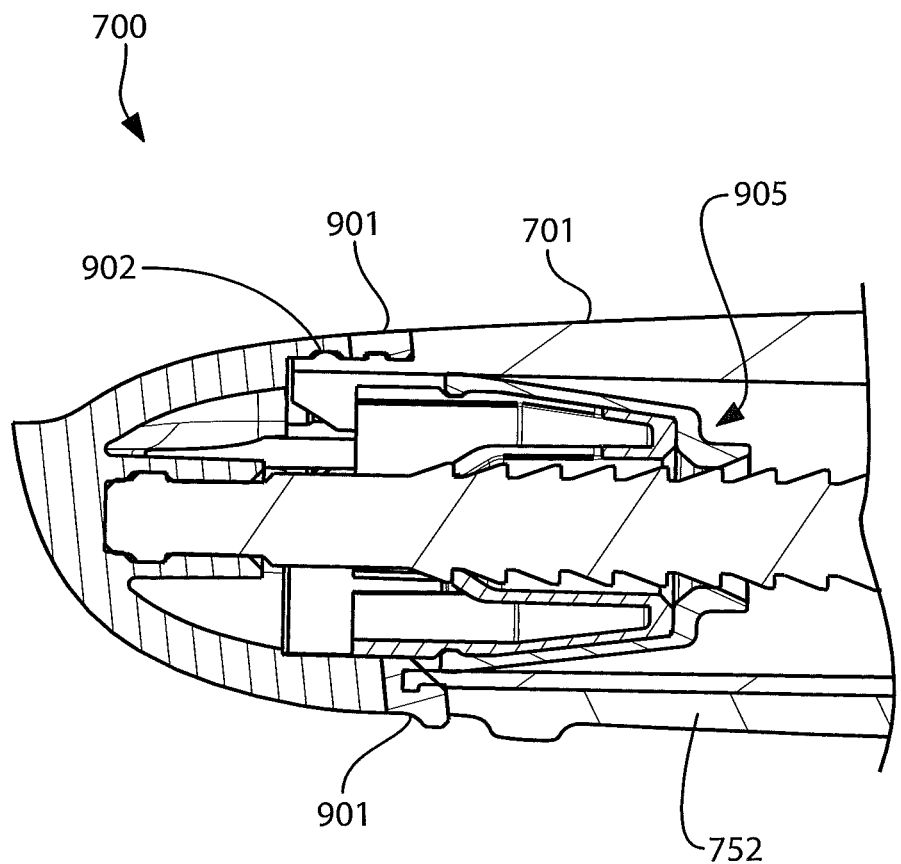
FIG. 27 is an enlarged partial side cross-sectional view of the proximal end portion of the dispenser of FIG. 26.

Referring to FIGS. 26, 27, and 34, the rear or proximal end 702 portion of dispenser 700 includes an attachable cap 900 that seals proximal end 702 of the dispenser. The cap 900 may be formed of a resilient elastomeric material in some embodiments and acts as a push-button to advance an internal rod 904 mechanism of the dispenser 700 and thereby release oral care agent through the applicator 709. The cap 900 compresses to perform the advancing function and then returns to its original shape. The cap also provides for user comfort both when toothbrush 600 is used in the brushing mode with dispenser 700 fully seated therein and when dispenser 700 is detached from the toothbrush for applying the oral care agent to the teeth. In one embodiment, the cap 900 preferably includes an annular flange 901 that engages an groove formed on the proximal or rear end of dispenser 700. The flange 901 is preferably made of a more rigid material than the cap 900 to advantageously provide a surface for pressing cap into position on dispenser 700 after the dispenser is filled with the oral care agent during the manufacturing process. The proximal end portion 702 of dispenser housing 701 may include one or more raised ridges 765 disposed near annular edge 764 that engages corresponding one or more annular grooves 902 (see FIG. 27) on the cap 900 for securing the cap and providing a leak resistant rear seal of the dispenser. In some embodiments, as shown, the axially forward extending rod 904 may be mounted on the cap 900 for further securing the cap to the dispenser housing 701. As best shown in FIG. 27, the rod 904 may include a plurality of axially spaced apart serrations which are configured to engage a retaining mechanism 905 disposed in the proximal end 702 of dispenser 700.

An exemplary method of using the toothbrush 600 and the dispenser 700 will now be briefly described. The dispenser 700 with the plug 650 is filled with an oral care material and inserted into a toothbrush 600. The toothbrush 600 with the dispenser 700 in the storage state as shown in FIG. 16 is provided for a user. The dispenser 700 is fully seated and secured in the toothbrush handle 610 as shown with a rear portion of the housing 701 near the proximal end 702 being lockingly engaged by the cantilevered top portion 660 of the handle 610 (via mounting tabs 801 and locking lugs 806 shown in FIGS. 31-33) and the distal dispensing end 703 being slidably frictionally engaged by the sheath portion 656 of the handle (see FIG. 29). After the user completes brushing his/her teeth with the toothbrush 600, or alternatively before brushing his/her teeth, the user grasps the dispenser housing 701 (preferably at grip portion 752 if provided) and pulls the proximal portion of the dispenser 700 near or at proximal end 702 outwards and away from toothbrush handle 610 by applying a force F initially in a direction generally transverse to longitudinal axis A-A. Since the distal dispenser end 703 is still seated in sheath portion 656 of toothbrush handle 610 (see, e.g. FIG. 29), this initial action applied by the user is a pivotal action with dispenser end acting as a pivot point. The rear or proximal half of to the dispenser will therefore pivot in an arcuate path initially away from toothbrush handle 610 (see, e.g. FIG. 16 and applied force F) at an angle with respect to the toothbrush handle and longitudinal axis A-A. Locking lugs 806 of dispenser housing 701 release mounting tabs 801 on toothbrush handle 610 (see FIGS. 31-33) and the mounting tabs are withdrawn from mounting recesses 800 of the dispenser housing. This uncouples the proximal end 702 of the dispenser 700 from toothbrush handle 610. The user may next unsheathe or withdraw the distal dispenser end 703 from sheath portion 656 of toothbrush handle 610 by sliding dispenser 700 rearward in a generally axial direction along the longitudinal axis A-A towards the rear or proximal end 612 of the handle. The plug 750 of the dispenser 700 adjacent to the applicator 709 is retained in the socket 654 in the toothbrush handle 610, thereby exposing the applicator. The user may then fully withdraw dispenser 700 from toothbrush 600 as shown in FIG. 17 which is now in the application state being fully uncoupled from the toothbrush. The user then applies the oral care agent to the teeth and/or other portions of the oral cavity as required with the applicator.

To reinsert the dispenser 700 back into toothbrush handle 610, the user simply repeats the foregoing steps in reverse. The dispenser 700 is then returned to the storage state shown in FIG. 16. It should be noted that whereas dispenser 300 is removed and reinserted from toothbrush 200 by applying only an axial force and motion to the dispenser, the dispenser 700 is removed from toothbrush 600 by a combination of forces and motions both transverse and axial as described above.

According to another aspect of the invention, the toothbrush handle 610 may further include a window 657 as best shown in FIG. 19. In a preferred exemplary embodiment, the window 657 may be comprised of a relatively clear and transparent insert 658 which is disposed in an aperture 659 in the handle 610 having a complementary shape to the insert. The window insert 658 may be formed as a separate piece and attached to handle 610 by any suitable means used in the art such as adhesives, heat or ultrasonic welding, or may be co-molded with the handle. Preferably, the window 657 is positioned on the toothbrush handle 610 so that at least a portion of the applicator 709 of dispenser 700 is visible through the window when the dispenser 700 is mounted in the handle 710. The window 657 communicates to the consumer/user that there is another product incorporated into the toothbrush 600. In some possible embodiments, different dispensers 700 may be available that contain different oral care agents or formulations (e.g. whitening, enamel protection, anti-sensitivity, flavors, etc.). The applicator 709 and/or distal dispensing end 703 of dispenser housing 701 may be color-coded and/or include indicia to correspond with a particular type of oral care agent formulation contained inside. This would allow the user to quickly identify which formulation is presently contained in the dispenser 700 seated in the toothbrush 600. Such different type dispensers 700 may be included in a kit as already described herein with reference to toothbrush 200 and dispenser 300.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. A method of applying an oral care agent to an oral surface comprising:
   providing a kit comprising at least one toothbrush and a dispenser containing an oral care agent, an applicator coupled to an end of the dispenser;
   delivering the oral care agent to the applicator; and
   applying the oral care agent to an oral surface using the applicator.

2. The method of claim 1 wherein the oral care agent is a tooth whitening agent.

3. The method of claim 1 wherein the oral care agent is an anti-sensitivity agent.

4. The method of claim 1 wherein applying the oral care agent to the oral surface comprises directly contacting the oral surface with the applicator.

5. The method of claim 1 wherein the oral care agent is delivered from the dispenser to the applicator via an orifice in a dispensing end of the dispenser.

6. The method of claim 1 wherein the oral surface is a tooth.

7. The method of claim 1 wherein the dispenser comprises a housing that extends from a proximal end to a dispensing end, the housing forming an internal chamber that defines a reservoir that contains the oral care agent.

8. The method of claim 7 wherein the applicator is coupled to the dispensing end of the housing.

9. The method of claim 1 wherein, prior to applying the oral care agent to the oral surface, the method comprises:
   applying a dentifrice to tooth cleaning elements extending from a head of the toothbrush;
   contacting teeth with the tooth cleaning elements in order to brush the teeth; and
   removing the head of the toothbrush from the mouth.

10. The method of claim 1 wherein the kit comprises the at least one toothbrush and a plurality of dispensers, each of the dispensers containing a different oral care agent.

* * * * *